United States Patent
Zhang et al.

(10) Patent No.: US 8,876,727 B2
(45) Date of Patent: Nov. 4, 2014

(54) PHRENIC NERVE STIMULATION DETECTION USING HEART SOUNDS

(75) Inventors: Xusheng Zhang, Shoreview, MN (US); Jeffrey M. Gillberg, Coon Rapids, MN (US); Thomas J. Mullen, Andover, MN (US); Paul J. DeGroot, Shoreview, MN (US)

(73) Assignee: Medtronic, Inc., Minneapolis, MN (US)

( * ) Notice: Subject to any disclaimer, the term of this patent is extended or adjusted under 35 U.S.C. 154(b) by 224 days.

(21) Appl. No.: 13/474,041

(22) Filed: May 17, 2012

(65) Prior Publication Data
US 2012/0296388 A1 Nov. 22, 2012

Related U.S. Application Data

(60) Provisional application No. 61/487,967, filed on May 19, 2011.

(51) Int. Cl.
```
A61B 5/04      (2006.01)
A61B 5/08      (2006.01)
A61N 1/36      (2006.01)
A61B 7/04      (2006.01)
A61B 5/00      (2006.01)
A61B 7/00      (2006.01)
A61B 5/0205    (2006.01)
A61N 1/365     (2006.01)
A61B 5/024     (2006.01)
```

(52) U.S. Cl.
CPC ............ *A61N 1/3611* (2013.01); *A61B 5/0826* (2013.01); *A61N 1/36135* (2013.01); *A61B 7/04* (2013.01); *A61B 5/0031* (2013.01); *A61B 7/005* (2013.01); *A61B 5/0205* (2013.01); *A61B 7/006* (2013.01); *A61N 1/36535* (2013.01); *A61N 1/36114* (2013.01); *A61N 1/36578* (2013.01); *A61B 5/4029* (2013.01); *A61B 5/7217* (2013.01); *A61B 5/024* (2013.01)
USPC ............... 600/528; 607/6; 607/20; 607/42

(58) Field of Classification Search
CPC .............. A61N 1/3601; A61N 1/3611; A61N 1/36114; A61N 1/36578; A61B 5/0205; A61B 5/08
USPC .............................. 607/6, 20, 28, 42; 600/528
See application file for complete search history.

(56) References Cited

U.S. PATENT DOCUMENTS

| | | |
|---|---|---|
| 4,374,382 A | 2/1983 | Markowitz |
| 5,117,824 A | 6/1992 | Keimel et al. |

(Continued)

OTHER PUBLICATIONS

Stec et al., "Premature ventricular complex-induced chronic cough and cough syncope," Eur Respir J. 2007:30 (2):391-394.

(Continued)

*Primary Examiner* — Carl H Layno
*Assistant Examiner* — Eugene Wu
(74) *Attorney, Agent, or Firm* — Michael C. Soldner

(57) ABSTRACT

A method and system of detecting phrenic nerve stimulation in a patient that includes detecting an activation event, obtaining a heart sound signal of a patient from an implanted heart sound sensor, determining that an electrical stimulation has been applied to the patient, in response to detecting the activation event, monitoring a portion of the heart sound signal, the portion defined by a predetermined window after the application of the electrical stimulation, and determining whether phrenic nerve stimulation occurred based on the portion of the heart sound signal.

22 Claims, 12 Drawing Sheets

(56) References Cited

U.S. PATENT DOCUMENTS

| | | | |
|---|---|---|---|
| 5,545,186 A | 8/1996 | Olson et al. | |
| 5,755,736 A | 5/1998 | Gillberg et al. | |
| 6,064,910 A * | 5/2000 | Andersson et al. | 607/20 |
| 6,393,316 B1 | 5/2002 | Gillberg et al. | |
| 6,415,183 B1 | 7/2002 | Scheiner et al. | |
| 6,449,508 B1 | 9/2002 | Sheldon et al. | |
| 6,643,548 B1 | 11/2003 | Mai et al. | |
| 7,123,962 B2 | 10/2006 | Siejko et al. | |
| 7,139,609 B1 | 11/2006 | Min et al. | |
| 7,209,786 B2 | 4/2007 | Brockway et al. | |
| 7,212,849 B2 | 5/2007 | Zhang et al. | |
| 7,248,923 B2 | 7/2007 | Maile et al. | |
| 7,343,915 B2 | 3/2008 | Addington et al. | |
| 7,363,086 B1 | 4/2008 | Koh et al. | |
| 7,460,909 B1 | 12/2008 | Koh et al. | |
| 7,689,283 B1 | 3/2010 | Schecter | |
| 7,787,946 B2 | 8/2010 | Stahmann et al. | |
| 2004/0220636 A1 | 11/2004 | Burnes | |
| 2005/0060002 A1* | 3/2005 | Zhu et al. | 607/19 |
| 2005/0080461 A1 | 4/2005 | Stahmann et al. | |
| 2006/0155202 A1* | 7/2006 | Arand et al. | 600/513 |
| 2006/0241711 A1* | 10/2006 | Sathaye | 607/28 |
| 2007/0049977 A1 | 3/2007 | Von Arx et al. | |
| 2007/0123943 A1 | 5/2007 | Patangay et al. | |
| 2007/0142866 A1 | 6/2007 | Li et al. | |
| 2007/0150014 A1 | 6/2007 | Kramer et al. | |
| 2007/0150017 A1 | 6/2007 | Salo | |
| 2008/0051839 A1 | 2/2008 | Libbus et al. | |
| 2008/0082018 A1 | 4/2008 | Sackner et al. | |
| 2008/0103399 A1 | 5/2008 | Patangay et al. | |
| 2008/0195168 A1 | 8/2008 | Arand et al. | |
| 2008/0234594 A1 | 9/2008 | Brooks et al. | |
| 2008/0262368 A1* | 10/2008 | Patangay et al. | 600/528 |
| 2008/0275349 A1 | 11/2008 | Halperin et al. | |
| 2008/0294060 A1* | 11/2008 | Haro et al. | 600/538 |
| 2008/0294213 A1 | 11/2008 | Holmstrom et al. | |
| 2009/0048640 A1 | 2/2009 | Bauer et al. | |
| 2009/0099621 A1 | 4/2009 | Lin et al. | |
| 2009/0131999 A1 | 5/2009 | Li et al. | |
| 2009/0210024 A1* | 8/2009 | M. | 607/28 |
| 2009/0216138 A1 | 8/2009 | Arand et al. | |
| 2009/0254139 A1 | 10/2009 | Bjorling | |
| 2010/0023078 A1 | 1/2010 | Dong et al. | |
| 2010/0069768 A1 | 3/2010 | Min et al. | |
| 2010/0073170 A1 | 3/2010 | Siejko et al. | |
| 2010/0087746 A1 | 4/2010 | Radzievsky et al. | |
| 2010/0185109 A1 | 7/2010 | Zhang et al. | |
| 2010/0198308 A1 | 8/2010 | Zhou et al. | |
| 2010/0312130 A1 | 12/2010 | Zhang et al. | |
| 2010/0331903 A1 | 12/2010 | Zhang et al. | |
| 2011/0015535 A1 | 1/2011 | Lange et al. | |
| 2011/0015703 A1 | 1/2011 | Ternes et al. | |
| 2011/0015704 A1 | 1/2011 | Ternes et al. | |
| 2011/0087079 A1 | 4/2011 | Aarts | |
| 2011/0245890 A1* | 10/2011 | Brisben et al. | 607/28 |

OTHER PUBLICATIONS

Toggweiler et al., "Visualizing Pacemaker-Induced Phrenic Nerve Stimulation with Acoustic Cardiography," PACE 2007;30:806-807.

Zuber et al., "Detection and Hemodynamic Significance of Cardiac Pacemaker-Induced Phrenic Nerve Stimulation," Congest Heart Fail. 2010:16:147-152.

Stahlberg et al., "Cardiac output response to changes of the atrioventricular delay in different body positions and during exercise in patients receiving cardiac resynchronization therapy," Europace (2009) 11: 1160-1167.

Zuber et al., "Systolic Dysfunction: Correlation of Acoustic Cardiography With Doppler Echocardiography," CHF. 2006; 12(4 supple 1): 14-18.

Auricchio et al., "Effect of Pacing Chamber and Atrioventricular Delay on Acute Systolic Function of Paced Patients With Congestive Heart Failure," Circulation 1999;99:2993-3001.

Baker, II et al., "Acute Evaluation of Programmer-Guided AV/PV and VV Delay Optimization Comparing an IEGM Method and Echocardiogram for Cardiac Resynchronization Therapy in Heart Failure Patients and Dual-Chamber ICD Implants," J Cardiovasc Electrophysiol, vol. 18, pp. 1-7, Jan. 2007.

Gold et al., "A Prospective Comparison of AV Delay Programming Methods for Hemodynamic Optimization during Cardiac Resynchronization Therapy," J Cardiovasc Electrophysiol, vol. 18, pp. 1-7, May 2007.

Gras et al., "Optimization of AV and VV Delays in the Real-World CRT Patient Population: An International Survey on Current Clinical Practice," PACE 2009;32:S236-239.

O'Donnell et al., "Long-Term Variations in Optimal Programming of Cardiac Resynchronization Therapy Devices," PACE 2005;28:S24-26.

Erne, "Beyond auscultation-acoustic cardiography in the diagnosis and assessment of cardiac disease," Swiss Med Wkly 2008;138(31-32):439-452.

U.S. Appl. No. 13/114,838, by Zhang et al., filed May 24, 2011.
U.S. Appl. No. 13/111,260, by Zhang et al., filed May 19, 2011.
U.S. Appl. No. 13/474,074, by Zhang et al., filed May 17, 2012.
U.S. Appl. No. 13/360,149, by Anderson et al., filed Jan. 27, 2012.
Office Action from U.S. Appl. No. 13/474,074, dated Feb. 28, 2014, 10 pp.
Response to Office Action dated Feb. 28, 2014, from U.S. Appl. No. 13/474,074, filed May 28, 2014, 13 pp.

\* cited by examiner

PHRENIC NERVE STIMULATION DETECTION USING HEART SOUNDS

RELATED APPLICATION

The present application claims priority and other benefits from U.S. Provisional Patent Application Ser. No. 61/487,967, filed May 19, 2011, entitled "PHRENIC NERVE STIMULATION DETECTION USING HEART SOUNDS", incorporated herein by reference in its entirety.

TECHNICAL FIELD

The invention relates to therapeutic electrical stimulation and physiological monitoring and, more particularly, to detection of phrenic nerve stimulation.

BACKGROUND

A wide variety of implantable medical devices for delivering a therapy or monitoring a physiologic condition have been clinically implanted or proposed for clinical implantation in patients. In some cases, implantable medical devices (IMD) deliver electrical stimulation therapy and/or monitor physiological signals via one or more electrodes or sensor elements, which may be included as part of one or more elongated implantable medical leads. Implantable medical leads are configured to allow one or more electrodes and/or sensors to be positioned at desired locations for sensing or delivery of stimulation. For example, electrodes or sensors are positioned at a distal portion of the lead and a connector is positioned at a proximal portion of the lead and coupled to an implantable medical device housing, which may contain electronic circuitry such as stimulation generation and/or sensing circuitry.

For example, implantable medical devices, such as cardiac pacemakers or implantable cardioverter defibrillators, provide therapeutic stimulation to the heart by delivering electrical therapy signals, such as pulses for pacing, or shocks for cardioversion or defibrillation, via electrodes of one or more implantable leads. In some cases, such an implantable medical device senses for intrinsic depolarizations of the heart, and controls the delivery of such signals to the heart based on the sensing. Upon detection of an abnormal rhythm, such as bradycardia, tachycardia or fibrillation, for example, an appropriate electrical signal or signals may be delivered to restore the normal rhythm. For example, in some cases, an implantable medical device delivers pacing, cardioversion, or defibrillation signals to the heart of the patient upon detecting ventricular tachycardia, and delivers defibrillation electrical signals to a patient's heart upon detecting ventricular fibrillation. Pacing signals typically have a lower energy than the cardioversion or defibrillation signals.

Pacing signals, cardioversion signals and defibrillation signals may affect tissue and nerves outside of the target tissue. For example, a pacing pulse applied to the left ventricle may also result in unintended phrenic nerve stimulation (PNS). In other examples, an electrical lead may be placed proximate to the phrenic nerve and provide stimulation designed to stimulate the phrenic nerve. During cardiac stimulation, PNS may cause unpleasant side effects for a patient, such as hiccups, dyspnea, uncomfortable muscle twitching and general malaise. PNS may also decrease the hemodynamic response to cardiac resynchronization therapy (CRT), or generally impair the hemodynamic performance of the heart, in the patient. When implanting a pacemaker, including lead placement, and setting pacing parameters (e.g., choosing the strength of stimulus), a physician or other clinician may attempt to detect and avoid PNS. In other instances, PNS may be provided as an additional therapy option for certain patients with a respiratory disorder.

Unintentional PNS has been reported in as many as 24% of patients with implanted CRT devices. Observation of PNS in hospitalized patients indicates that some instances of unintentional PNS are asymptomatic, e.g., not perceived by the patient or detectable via routine observation of the patient. Unintended movements of the diaphragm can be confirmed through fluoroscopy in the absence of recognizable symptoms for the patient. Although asymptomatic PNS may not lead to obvious side effects such as hiccups, it may still affect the hemodynamics of a patient.

SUMMARY

In general, the disclosure is directed to detection of phrenic nerve stimulation (PNS) using an implanted heart sounds sensor. In some examples, pacing-induced phrenic nerve stimulation is detected using the techniques described herein. In some examples, asymptomatic phrenic nerve stimulation is detected. In some examples, intentional, e.g., therapeutic, PNS is detected using the techniques described herein, e.g., to evaluate whether PNS has been achieved or the efficacy of PNS.

In one example, the disclosure is directed to a method in which phrenic nerve stimulation is detected by obtaining a heart sound signal from an implanted heart sound sensor, obtaining a signal indicating an electrical stimulation has been applied and initiating a detection sequence, the detection sequence including: filtering the heart sound signal, monitoring a portion of the heart sound signal, the portion defined by a window after an applied stimulation and before heart sound S1, and determining whether phrenic nerve stimulation occurred based on the portion of the heart sound signal. In certain more specific examples, the detection sequence is initiated in response to an activation event. The activation event may indicate that certain predetermined conditions have been met.

In another example, the disclosure is directed to a system for detecting phrenic nerve stimulation, including an implantable heart sound sensor configured to obtain a heart sound signal, and provide the heart sound signal to a processor. The processor is configured to obtain a signal indicating an electrical stimulation has been applied, initiate a detection sequence including: filtering the heart sound signal, monitoring a portion of the heart sound signal, the portion defined by a window after an applied stimulation and before heart sound S1, and determining whether phrenic nerve stimulation occurred based on the portion of the heart sound signal.

The details of one or more examples are set forth in the accompanying drawings and the description below. Other features, objects, and advantages will be apparent from the description and drawings, and from the claims.

DETAILED DESCRIPTION

Figure 1:
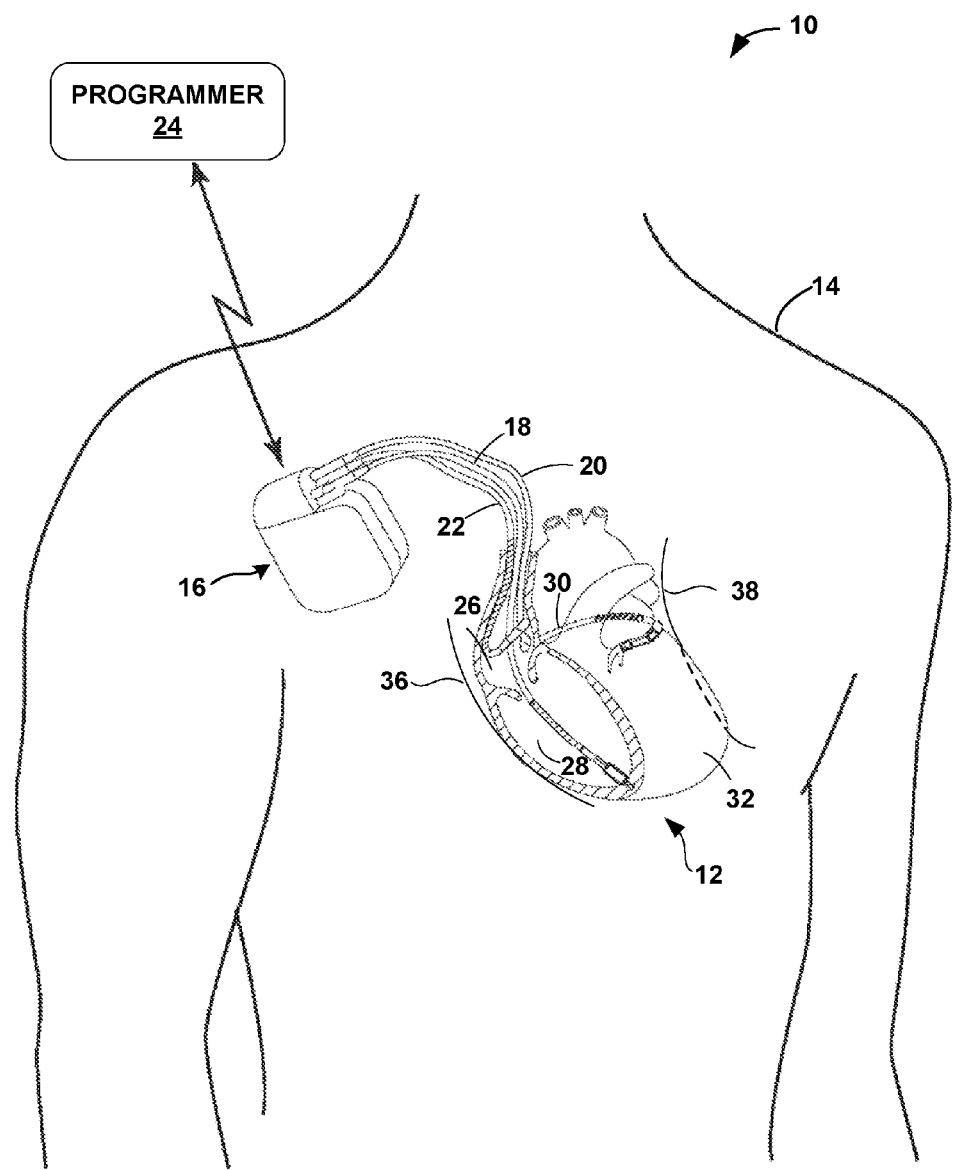
FIG. 1 is a conceptual diagram illustrating an example system that detects phrenic nerve stimulation, consistent with an example of the present disclosure.

The techniques described in this disclosure may allow a medical device to detect the presence of phrenic nerve stimulation. In some examples, the phrenic nerve stimulation is an unintended side effect of electrical stimulation applied to a patient's heart. In other examples, the detected phrenic nerve stimulation may be purposeful. For example, phrenic nerve stimulation may be used to treat neurological disorders affecting mechanical ventilation. In various examples, the detection of phrenic nerve stimulation occurs in response to an activation event.

The activation event may be a change in the electrical stimulation applied to the patient's heart. In other examples, the activation event may be a posture or activity level of the patient detected by a posture or activity sensor. For example, an activation event may be an indication that the patient is lying down. In other examples, the activation event may be the detection of low activity of the patient. In some examples, the activation event may be the detection of combination of factors. For example, an activation event may be on the occurrence of a particular posture or activity in conjunction with a change in the electrical stimulation. In other examples, the activation event may be based on time. For example, an activation event may be the passage of predetermined amount of time since the previous phrenic nerve detection sequence. In still other examples, the activation event may be on the occurrence of a particular time of day.

As used herein, the term heart sound refers to a feature of a heart sound signal, such as the S1, S2, S3, or S4 heart sounds. There may be multiple heart sounds, e.g., each of an S1, S2, S3 and S4 heart sound, for any given cardiac cycle or heart beat. In some examples, the medical device classifies a heart beat or cardiac cycle as normal or abnormal based on the classifications for one or more heart sounds detected during the heart beat or cardiac cycle. In such examples, the medical device may confirm that a cardiac rhythm is treatable when one or more heart beats are classified as abnormal, or withhold therapy when one or more heart beats are classified as normal. In other examples, the heart sound signal may include signals representing other acoustic occurrences including, for example, diaphragm movement in response to phrenic nerve stimulation.

Pacing-induced phrenic nerve stimulation, both symptomatic and asymptomatic, may cause unpleasant symptoms and decreased hemodynamic performance for the patient. In various examples consistent with the present disclosure, phrenic nerve stimulation may be both detected, and in response to the detection, avoided in the future.

Pacing-induced phrenic nerve stimulation is of particular concern when pacing is provided by a left-ventricular lead, such as a left-ventricular quadrapolar lead. This is because a left-ventricular lead may position one or more electrodes in close proximity to the left phrenic nerve. A physician may desire to program the IMD to provide cardiac resynchronization therapy, including left-ventricular pacing, that provides heart function as close to normal while avoiding capturing one or more phrenic nerves with the applied pulses.

In some examples, the disclosure is directed to detecting pacing-induced PNS using heart sounds, and in response, reprogramming the IMD to provide CRT in a manner that does not capture the phrenic nerve. In some examples, reprogramming the IMD includes changing one or more pacing vectors to avoid phrenic nerve stimulation. In some examples, reprogramming the IMD includes modifying various pacing parameters such as pulse strength to avoid phrenic nerve stimulation, with or without changing the pacing vectors. In some examples, modification of the pulse strength is first attempted and, if phrenic nerve stimulation is not avoided without compromising cardiac capture, modification of the pacing vector is attempted. The determination of new pulse strength or pacing vector may be made based on information extracted from the heart sounds signal. This is possible because heart sound sensors can detect diaphragmatic muscular movement caused by both symptomatic and asymptomatic PNS in the form of a sound artifact.

As discussed in more detail below with respect to the various figures, both symptomatic and asymptomatic PNS may be detected using heart sounds. In various examples, IMD is not continuously monitoring heart sounds for PNS. Instead, a detection sequence may be initiated at a given time of day, for example. This allows the IMD to save battery power and to perform other functions using the same sensors and processors at other times. In some examples, PNS detection is initiated at times that PNS is most likely to be detected. For example, a PNS detection sequence may be initiated when a patient is lying on his or her left side. In instances where a left-ventricular lead is used to deliver cardiac pacing, phrenic nerve stimulation may occur when the patient is on his or her left side, but not when the patient is in other positions.

For pacing induced PNS, the IMD may check for the presence of a PNS artifact just after delivery of a ventricular pacing pulse. In some examples, the IMD looks for the PNS artifact within 80 milliseconds (ms) of the pulse being applied. In other examples, the IMD looks for PNS to occur between the ventricular pacing pulse and the first heart sound, S1.

In an attempt to avoid PNS when setting pacing parameters, the IMD may step up the pacing pulse amplitude and/or width from the minimal pacing capture threshold to the maximum output of the IMD. In some examples, the IMD may stop the stepping up process when PNS is detected. In some examples where PNS detection is implemented after the pacing parameters have been set, the IMD steps down the amplitude of the pacing pulse after an initial determination of PNS until PNS is not longer detected, so long as cardiac capture is maintained.

In some examples, it may be desirable to determine if a preferred or chosen pacing vector or modality will cause PNS for a specific patient. This may be done by first applying pacing stimulation at the maximum output of the stimulation generator to see if PNS is present or not. If PNS is present, then the IMD may gradually step-down the pacing pulse amplitude until the minimal pacing amplitude that still causes PNS is determined (PNS threshold). If the PNS threshold is above the threshold for capturing the ventricle to provide adequate pacing, then the chosen pacing vector may still be used. If not, then another vector or electrode configuration may be tested until one is found where a pacing pulse may be delivered that provides pacing capture without also stimulating the phrenic nerve.

In some examples, once PNS is detected, the IMD, or another device that communicates with the IMD, may modify the pacing parameters to provide pacing that does not compromise the patient's hemodynamics while avoiding PNS. In some examples, the heart sound signal is used to assess the pacing parameters not only for PNS but for overall heart function.

In some examples, phrenic nerve stimulation may be desired. For example, it may be desirable to provide PNS as a substitute for mechanical ventilation in patients with neurological disorders such as central sleep apnea. In such examples, the amount of stimulation applied may be different every few pulses in order to simulate normal breathing patterns. PNS detection using heart sounds may be used to confirm the effectiveness of the attempted phrenic nerve stimulation.

FIG. 1 is a conceptual diagram illustrating an example system 10 that may detect phrenic nerve stimulation. In some examples, system 10 monitors both cardiac electrical activity and heart sounds-based signals. In some examples, system 10 provides stimulation to the cardiac tissue based on a set of parameters, and monitors a signal representative of cardiac electrical activity, e.g., an electrogram (EGM), and a heart sounds signal. Based at least on the heart sounds signal, system 10 determines whether the cardiac stimulation at the present stimulation parameters is causing unwanted phrenic nerve stimulation. In various examples, a phrenic nerve detection sequence is initiated in response to an activation event.

System 10 includes implantable medical device (IMD) 16, which is connected to leads 18, 20 and 22 and is optionally communicatively coupled to programmer 24. IMD 16 senses electrical signals attendant to the depolarization and repolarization of heart 12, e.g., a cardiac EGM, via electrodes on one or more leads 18, 20 and 22 or the housing of IMD 16. In some examples, IMD 16 also delivers cardiac therapy in the form of electrical signals to heart 12 via electrodes located on one or more leads 18, 20 and 22 or a housing of IMD 16. The cardiac therapy may be pacing, cardioversion and/or defibrillation pulses. The IMD 16 may also provide respiratory induction therapy. The respiratory induction therapy includes electrical stimulation to one or more phrenic nerves 36 and 38 via electrodes located on one or more of leads 18, 20 and 22, other leads not illustrated in FIG. 1, or a housing of IMD 16. In some examples, the electrodes used to stimulate phrenic nerves 36 and 38 may be used for both cardiac and phrenic nerve stimulation. IMD 16 also includes one or more heart sound sensors (not shown in FIG. 1) used to detect the occurrence of phrenic nerve stimulation in patient 14. IMD may similarly include or be coupled to other sensors, such as one or more accelerometers, for detecting other physiological parameters of patient 14, such as activity or posture.

In some examples, programmer 24 takes the form of a handheld computing device, computer workstation or networked computing device that includes a user interface for presenting information to and receiving input from a user. A user, such as a physician, technician, surgeon, electro-physiologist, or other clinician, may interact with programmer 24 to retrieve physiological or diagnostic information from IMD16. A user may also interact with programmer 24 to program IMD 16, e.g., select values for operational parameters of the IMD or initiate a phrenic nerve stimulation detection sequence.

IMD 16 and programmer 24 may communicate via wireless communication using any techniques known in the art. Examples of communication techniques may include, for example, low frequency or radiofrequency (RF) telemetry. Other techniques are also contemplated. In some examples, programmer 24 may include a programming head that may be placed proximate to the patient's body near the IMD 16 implant site in order to improve the quality or security of communication between IMD 16 and programmer 24. In other examples, programmer 24 may be located remotely from IMD 16, and communicate with IMD 16 via a network.

Leads 18, 20, 22 extend into the heart 12 of patient 14 to sense electrical activity of heart 12 and/or deliver electrical stimulation to heart 12. The leads may also deliver electrical stimulation to phrenic nerve 38. In the example shown in FIG. 1, right ventricular (RV) lead 18 extends through one or more veins (not shown), the superior vena cava (not shown), and right atrium 26, and into right ventricle 28. Left ventricular (LV) coronary sinus lead 20 extends through one or more veins, the vena cava, right atrium 26, and into the coronary sinus 30 to a region adjacent to the free wall of left ventricle 32 of heart 12. Right atrial (RA) lead 22 extends through one or more veins and the vena cava, and into the right atrium 26 of heart 12. In some examples, RA lead 22 may be used to stimulate right phrenic nerve 36. In some examples, LV coronary sinus lead 20 may be used to stimulate left phrenic nerve 38.

Techniques for detecting stimulation of one or more of phrenic nerves 36 and 38 are primarily described herein as being performed by IMD 16, e.g., by a processor of IMD 16. In other examples, some or all of the functions ascribed to IMD 16 or a processor thereof may be performed by one or more other devices such as programmer 24, or a processor thereof. For example, IMD 16 may process cardiac and/or heart sound signals to determine whether therapy should continue to be delivered based on current parameters, or whether adjustments to the parameters should be made, and control the parameters used by IMD 16 to deliver the therapy. Alternatively, programmer 24 may process cardiac and/or heart sound signals received from IMD 16 to determine whether therapy should continue to be delivered based on current parameters or whether adjustments to the parameters should be made, and control according to what parameters IMD 16 delivers the therapy. Furthermore, although described herein with respect to an IMD, in other examples, the techniques described herein may be performed or implemented in an external medical device, which may be coupled to a patient via percutaneous or transcutaneous leads. In some examples, various functions of IMD 16 may be carried out by multiple IMDs in communication with one another.

Figure 2:
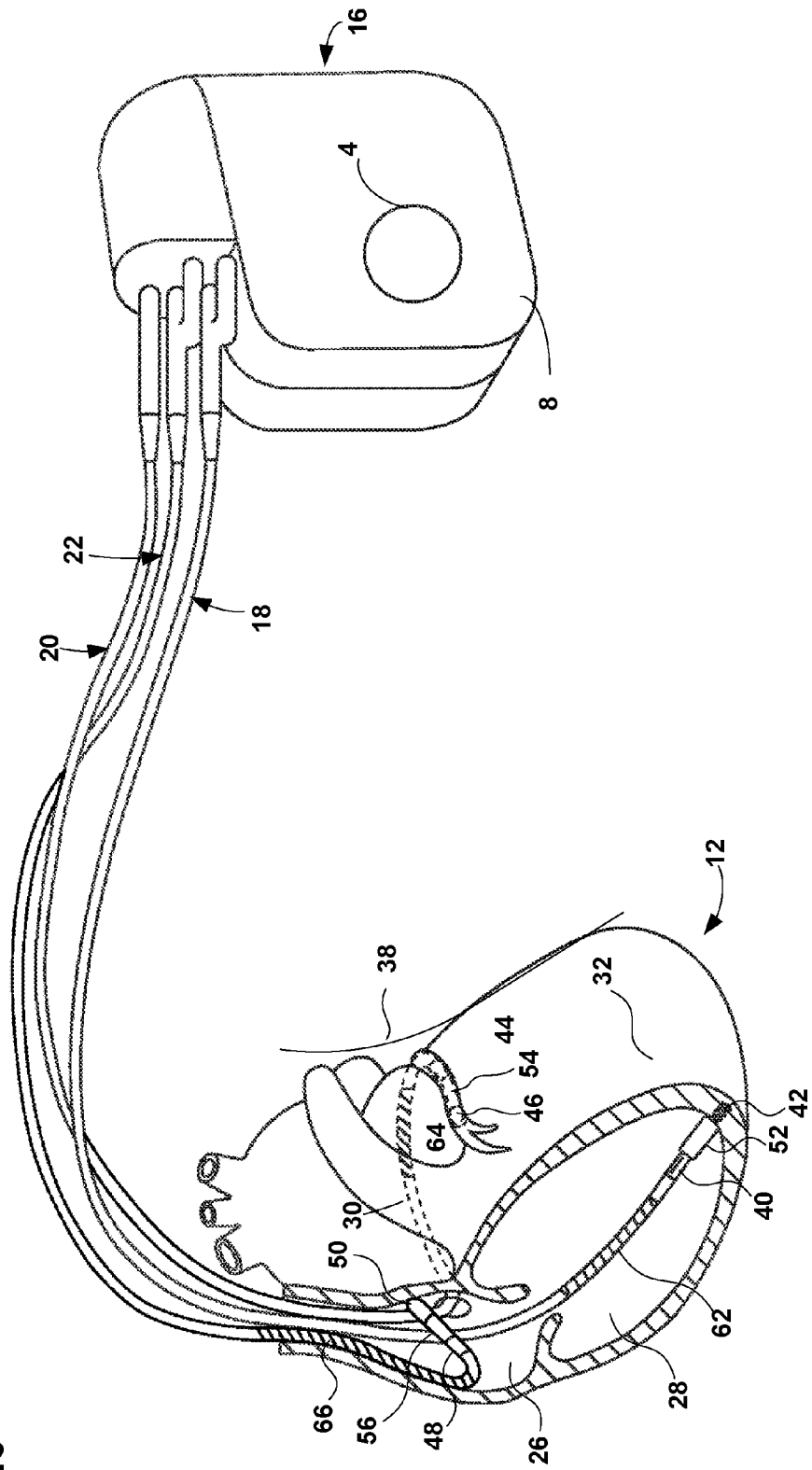
FIG. 2 is a conceptual diagram illustrating the implantable medical device (IMD) and leads of the system shown in FIG. 1 in greater detail.

FIG. 2 is a conceptual diagram illustrating IMD 16 and leads 18, 20 and 22 of system 10 in greater detail. In the illustrated example, bipolar electrodes 40 and 42 are located adjacent to a distal end of lead 18. In addition, bipolar electrodes 44 and 46 are located adjacent to a distal end of lead 20, and bipolar electrodes 48 and 50 are located adjacent to a distal end of lead 22. In alternative examples, not shown in FIG. 2, one or more of leads 12, 20 and 22, such as left-ventricular lead 20, may include quadrapole electrodes located adjacent to a distal end of the lead.

In the illustrated example, electrodes 40, 44 and 48 take the form of ring electrodes, and electrodes 42, 46 and 50 may take the form of extendable helix tip electrodes mounted retractably within insulative electrode heads 52, 54 and 56, respectively. Leads 18, 20, 22 also include elongated electrodes 62, 64, 66, respectively, which may take the form of a coil. In some examples, each of electrodes, 40, 42, 44, 46, 48, 50, 62, 64 and 66 is electrically coupled to a respective conductor within the lead body of its associated lead 18, 20, 22, and thereby coupled to circuitry within IMD 16.

In some examples, IMD 16 includes one or more housing electrodes, such as housing electrode 4 illustrated in FIG. 2, which may be formed integrally with an outer surface of hermetically-sealed housing 8 of IMD 16 or otherwise coupled to housing 8. In some examples, housing electrode 4 is defined by an uninsulated portion of an outward facing portion of housing 8 of IMD 16. Other divisions between insulated and uninsulated portions of housing 8 may be employed to define two or more housing electrodes. In some examples, a housing electrode comprises substantially all of housing 8.

As described in further detail with reference to FIG. 3, housing 8 encloses a signal generator that generates therapeutic stimulation, such as cardiac pacing, cardioversion and defibrillation pulses, as well as a sensing module for sensing electrical signals attendant to the depolarization and repolarization of heart 12. IMD 16 may also include a heart sounds sensor that monitors acoustic noises including heart sounds and sounds resulting from phrenic nerve stimulation, for example. The heart sounds sensor may be, for example, an accelerometer or a microphone. The heart sounds sensor may be enclosed within housing 8. Alternatively, the heart sounds sensor may be integrally formed with or carried on an outer surface of housing 8, carried on or within a lead coupled to IMD 16, such as one or more leads 18, 20 and 22, or be a separate, remote sensor that wirelessly communicates with IMD 16, programmer 24 or any other device described herein.

IMD 16 senses electrical signals attendant to the depolarization and repolarization of heart 12 via electrodes 4, 40, 42, 44, 46, 48, 50, 62, 64 and 66. IMD 16 may sense such electrical signals via any bipolar combination of electrodes 40, 42, 44, 46, 48, 50, 62, 64 and 66. Furthermore, any of the electrodes 40, 42, 44, 46, 48, 50, 62, 64 and 66 may be used for unipolar sensing in combination with housing electrode 4.

In some examples, IMD 16 delivers stimulating pulses via bipolar combinations of electrodes chosen based on EGM signals and/or heart sound signals as analyzed by a signal analyzer within IMD. For example, bipolar combinations of electrodes 40, 42, 44, 46, 48, and 50 are used to produce depolarization of cardiac tissue of heart 12. In addition, phrenic nerve stimulation pulses may be delivered by various electrodes used to provide cardiac stimulation, and which electrodes may be chosen to deliver phrenic nerve stimulation based on the location of the electrodes. In some examples, IMD 16 delivers stimulation to either cardiac tissue or the phrenic nerve via any of electrodes 40, 42, 44, 46, 48 and 50 in combination with housing electrode 4 in a unipolar configuration. In some examples, the choice of electrodes delivering cardiac and phrenic nerve electrical stimulation may be based on default settings. Furthermore, IMD may deliver cardioversion or defibrillation pulses to heart 12 or pulses to phrenic nerves 36 and 38 via any combination of elongated electrodes 62, 64, 66 and housing electrode 4.

The illustrated numbers and configurations of leads 18, 20 and 22 and electrodes are merely examples. Other configurations, i.e., numbers and positions of leads and electrodes, are possible. In some examples, system 10 may include an additional lead or lead segment having one or more electrodes positioned at different locations in the cardiovascular system for sensing and/or delivering therapy to patient 14. For example, instead of or in addition to intracardiac leads 18, 20 and 22, system 10 may include one or more epicardial or subcutaneous leads not positioned within the heart. For example, a lead may be positioned to provide one or more electrodes in proximity to or in contact with phrenic nerve 36 or phrenic nerve 38. As another example, system 10 may include an additional lead that carries a heart sound sensor positioned such that signals generated by the heart sounds sensor include information regarding a patient's respiratory activity including, for example, inspiration and expiration.

Figure 3:
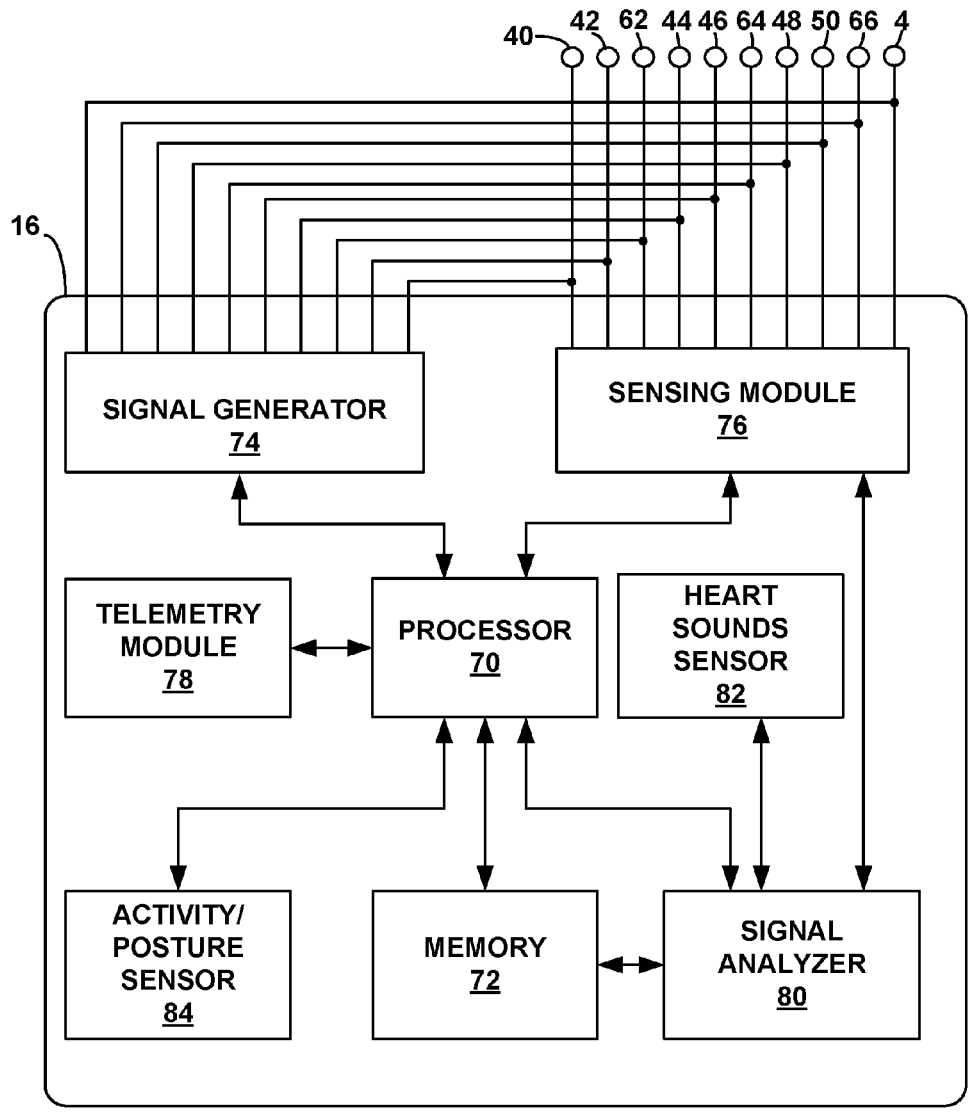
FIG. 3 is a block diagram illustrating an example configuration of the IMD of FIG. 1.

FIG. 3 is a block diagram illustrating an example configuration of IMD 16. In the illustrated example, IMD 16 includes a processor 70, memory 72, signal generator 74, sensing module 76, telemetry module 78, a signal analyzer 80, a heart sounds sensor 82, and an activity/posture sensor 84. Memory 72 includes computer-readable instructions that, when executed by processor 70, cause IMD 16 and processor 70 to perform various functions attributed to IMD 16 and processor 70 herein. Memory 72 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 70 may include any one or more of a microprocessor, a controller, a digital signal processor (DSP), an application specific integrated circuit (ASIC), a field-programmable gate array (FPGA), or equivalent discrete or analog logic circuitry. In some examples, processor 70 may include multiple components, such as any combination of one or more microprocessors, one or more controllers, one or more DSPs, one or more ASICs, or one or more FPGAs, as well as other discrete or integrated logic circuitry. The functions attributed to processor 70 herein may be embodied as software, firmware, hardware or any combination thereof. Generally, processor 70 controls signal generator 74 to deliver stimulation therapy to heart 12 of patient 14 according to a selected one or more of therapy programs or parameters, which may be stored in memory 72. As an example, processor 70 may control signal generator 74 to deliver electrical pulses with the amplitudes, pulse widths, frequency, or electrode polarities specified by the selected one or more therapy programs. The therapy programs may be selected by the processor 70 based on information from the signal analyzer 80.

Signal generator 74 is configured to generate and deliver electrical stimulation therapy to patient 12. As shown in FIG. 3, signal generator 74 is electrically coupled to electrodes 4, 40, 42, 44, 46, 48, 50, 62, 64 and 66, e.g., via conductors of the respective leads 18, 20, and 22 and, in the case of housing electrode 4, within housing 8. For example, signal generator 74 may deliver stimulating pulses to phrenic nerves 36 and 38 via at least two of electrodes 4, 40, 42, 44, 46, 48, 50, 62, 64 and 66. In addition, in some examples, signal generator 74 may deliver pacing pulses, defibrillation shocks or cardioversion shocks to heart 12 via at least two of electrodes 4, 40, 42, 44, 46, 48, 50, 62, 64 and 66. In some examples, signal generator 74 delivers stimulation in the form of signals other than pulses such as sine waves, square waves, or other substantially continuous time signals.

Signal generator 74 may include a switch module (not shown) and processor 70 may use the switch module to select, e.g., via a data/address bus, which of the available electrodes are used to deliver the electrical stimulation. The switch module may include a switch array, switch matrix, multiplexer, or any other type of switching device suitable to selectively couple stimulation energy to selected electrodes. Electrical sensing module 76 monitors electrical cardiac signals from any combination of electrodes 4, 40, 42, 44, 46 48, 50, 62, 64, and 66. Sensing module 76 may also include a switch module which processor 70 controls to select which of the available electrodes are used to sense the heart activity, depending upon which electrode combination is used in the current sensing configuration.

Sensing module 76 may include one or more detection channels, each of which may comprise an amplifier. The detection channels may be used to sense the cardiac signals. Some detection channels may detect events, such as R-waves or P-waves, and provide indications of the occurrences of such events to processor 70 and/or signal analyzer 80. One or more other detection channels may provide the signals to an analog-to-digital converter, for conversion into a digital signal for processing or analysis by processor 70 or signal analyzer 80.

For example, sensing module 76 may comprise one or more narrow band channels, each of which may include a narrow band filtered sense-amplifier that compares the detected signal to a threshold. If the filtered and amplified signal is greater than the threshold, the narrow band channel indicates that a certain electrical cardiac event, e.g., depolarization, has occurred. Processor 70 then uses that detection in measuring frequencies of the sensed events. Signal analyzer 80 may use the detection in connection with sensed heart sounds to determine one or more cardiac metrics.

In one example, at least one narrow band channel may include an R-wave or P-wave amplifier. In some examples, the R-wave and P-wave amplifiers may take the form of an automatic gain controlled amplifier that provides an adjustable sensing threshold as a function of the measured R-wave or P-wave amplitude. Examples of R-wave and P-wave amplifiers are described in U.S. Pat. No. 5,117,824 to Keimel et al., which issued on Jun. 2, 1992 and is entitled, "APPARATUS FOR MONITORING ELECTRICAL PHYSIOLOGIC SIGNALS," and is incorporated herein by reference in its entirety.

In some examples, sensing module 76 includes a wide band channel which may comprise an amplifier with a relatively wider pass band than the narrow band channels. Signals from the electrodes that are selected for coupling to the wide-band amplifier may be converted to multi-bit digital signals by an analog-to-digital converter (ADC) provided by, for example, sensing module 76, processor 70, or signal analyzer 80. Processor 70 may analyze the digitized version of signals from the wide band channel. Processor 70 may employ digital signal analysis techniques to characterize the digitized signals from the wide band channel to, for example, detect and classify the patient's heart rhythm. In some examples, the signal analyzer 80 employs digital signal analysis techniques to characterize the digitized signals from the wide band channel. The digitized signals may be used in conjunction with heart sound signals to determine if phrenic nerve stimulation has occurred.

Processor 70 may initiate a phrenic nerve stimulation detection sequence in response to detecting an activation event. In some examples, processor 70 may receive an activation signal from programmer 24 via telemetry module 78, which may be the activation event, before initiating phrenic nerve stimulation detection. In some examples, the activation event may be one or more of an activity/posture detected via activity posture sensor 84, signal analyzer 80, memory 72, and sensing module 76. In some examples, processor 70 may initiate phrenic nerve stimulation detection at a given time. For example, memory 72 may provide a program to processor 70 wherein phrenic nerve stimulation detection occurs every day at a predetermined time. In such cases the activation event is the time of day. In other examples, processor 70 may initiate phrenic nerve stimulation detection during a predetermined time range when predefined parameters are met. For example, processor 70 may initiate phrenic nerve stimulation detection between 10 p.m. and 5 a.m. when an activation event, such as activity/posture sensor 84 indicating that patient 12 is lying down, occurs. In some specific examples, processor 70 may initiate phrenic nerve stimulation detection in response to an activation event such as an indication from the activity/posture sensor 84 that patient 12 is lying on his or her left side is received. In some examples, processor 70 may initiate a phrenic nerve stimulation detection sequence based on an activation event such as one or more pacing parameters changing. In some examples, processor 70 may initiate a phrenic nerve stimulation detection sequence in conjunction with a pacing parameter optimization process.

In the example in FIG. 3 (e.g., to detect the presence of phrenic nerve stimulation), IMD 16 also includes heart sound sensor 82 and signal analyzer 80. Heart sound sensor 82 generates an electrical signal based on sensed acoustics or vibrations originating from heart movement and diaphragm movement, for example. In some examples, heart sound sensor 82 may comprise more than one sensor. For example, the heart sound sensor may include multiple individual sensors. In some examples, heart sound sensor 82 is an acoustic sensor, such as an accelerometer, microphone, or piezoelectric device. The acoustic sensor picks up sounds resulting from the activation of the diaphragm in addition to the heart sounds S1-S4.

In the illustrated example of FIG. 3, heart sensor 82 is enclosed within housing 8 of IMD 16. In some examples, heart sounds sensor 82 may be formed integrally with or on an outer surface of housing 8. In some examples, heart sounds sensor 82 is located on one or more leads that are coupled to IMD 16 or may be implemented in a remote sensor that wirelessly communicates with IMD 16. In such cases, heart sounds sensor 82 may be electrically or wirelessly coupled to circuitry contained within housing 8 of IMD 16. In some examples, a remote heart sound sensor 82 may be wirelessly connected to programmer 24.

Signal analyzer 80 receives the electrical signal generated by heart sounds sensor 82. In one example, signal analyzer 80 may process the sensor signal generated by heart sounds sensor 82 to detect occurrences of phrenic nerve stimulation. In some examples, signal analyzer 80 processes the heart sound sensor signal to generate an envelope signal, detect occurrences of phrenic nerve stimulation, detect other hearts sounds, extract heart sound features from the detected heart sound signal, and assess various cardiac metrics. The cardiac metrics may provide a method to assess the electrical-mechanical functioning of the heart 12. In some examples, the detected heart sounds features, both those associated with phrenic nerve stimulation, and those associated with other heart activity, may be compared to values for each feature stored in memory 72. The heart sound features may then be classified based on the deviation from the stored values. The heart sound features and/or their classifications may be used to determine whether phrenic nerve stimulation has occurred, and to assess the function of heart 12.

In some examples the classified respiratory features are used by the signal analyzer along with EGM information extracted from an EGM signal collected by the sensing module 76. In some examples, the EGM information may be extracted by the sensing module 76 and provided to processor 70. The EGM information may then be provided to the signal analyzer 80 by memory 72 or processor 70. In some examples, the unprocessed signal is provided to processor 70 by sensing module 76 for information extraction. In some examples, the EGM information may also be extracted from the EGM signal by the signal analyzer 80. Examples of the operation of signal analyzer 80 and processor 70 in accordance with these example methods are described in greater detail with respect to FIGS. 6-8.

A heart sound based indication may be output from signal analyzer 80 to processor 70. In some examples, the heart sound features are output to the processor 70. The processor 70 may determine whether phrenic nerve stimulation has occurred based on the information received from signal analyzer 80. In some examples, processor may adjust stimulation provided by signal generator 74 based on the heart sounds-based information received.

In various examples one or more of the functions attributed to signal analyzer 80 may be performed by processor 70. In some examples, signal analyzer 80 may be implemented as hardware, software, or some combination thereof. For example, the functions of signal analyzer 80 described herein may be implemented in a software process executed by processor 70.

Figure 4:
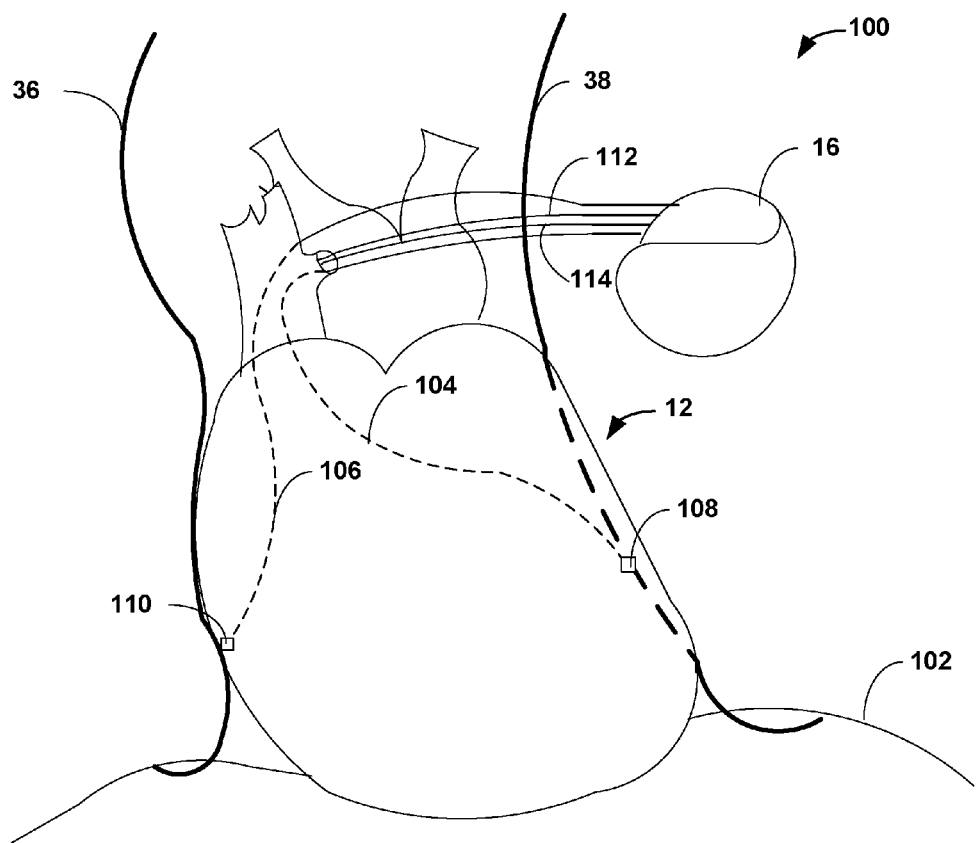
FIG. 4 is a conceptual diagram illustrating an example system that delivers phrenic nerve stimulation, consistent with an example of the present disclosure.

FIG. 4 is a conceptual diagram illustrating an example system 100 for detecting phrenic nerve stimulation using heart sounds. The system 100 includes IMD 16 that monitors heart sounds based signals and determines if the phrenic nerve is being stimulated based on the heart sounds-based signal. In some examples IMD 16 may also monitor cardiac electrical activity signals, e.g., EGM signals, and may provide cardiac tissue stimulation. In some examples, the detection of phrenic nerve stimulation may trigger an optimization protocol for the pacing parameters used to provide the cardiac tissue stimulation. In some examples, the system 100 detects the occurrence of phrenic nerve stimulation and provides an indication of the phrenic nerve stimulation to a remote device, for example, programmer 24.

System 100 includes IMD 16, which is connected to leads 104, 106, 112 and 114, and is optionally communicatively coupled to a programmer (not shown in FIG. 4). IMD 16 senses various signals attendant to activation of diaphragm 102 in response to electrical stimulation of phrenic nerves 36 and 38. In some examples, leads 104 and 106 are positioned proximate to the phrenic nerves. The stimulation may be provided to phrenic nerves 36 and 38 via electrodes 108 and 110. Leads 104 and 106 may be intracardiac leads including additional electrodes (not shown) providing cardiac stimulation, and leads 112 and 114 may be intracardiac leads, e.g., for providing cardiac stimulation. In some examples, electrodes 108 and 110 may be cuff electrodes that at least partially surround phrenic nerves 36 and 38, respectfully.

In some examples, IMD 16 senses electrical signals attendant to the depolarization and repolarization of heart 12, e.g., a cardiac EGM, via electrodes on one or more of leads 104, 106, 112 and 114, or the housing of IMD 16. In some examples, IMD 16 delivers cardiac therapy in the form of electrical signals to heart 12 via electrodes located on one or more of leads 104, 106, 112 and 114. IMD may also include, or be coupled to, other sensor such as one or more accelerometers for detecting other physiological parameters of a patient, such as activity or posture.

Techniques for monitoring stimulation of one or more of phrenic nerves 36 and 38 are primarily described herein as being performed by IMD 16, e.g., by a processor of IMD 16. For example, IMD 16 may process respiratory-based signals to determine whether the IMD 16 should continue to deliver based on current parameters, or whether adjustments to the parameters should be made. The processor in IMD 16 may also control the parameters used by 16 to deliver therapy.

Figure 5:
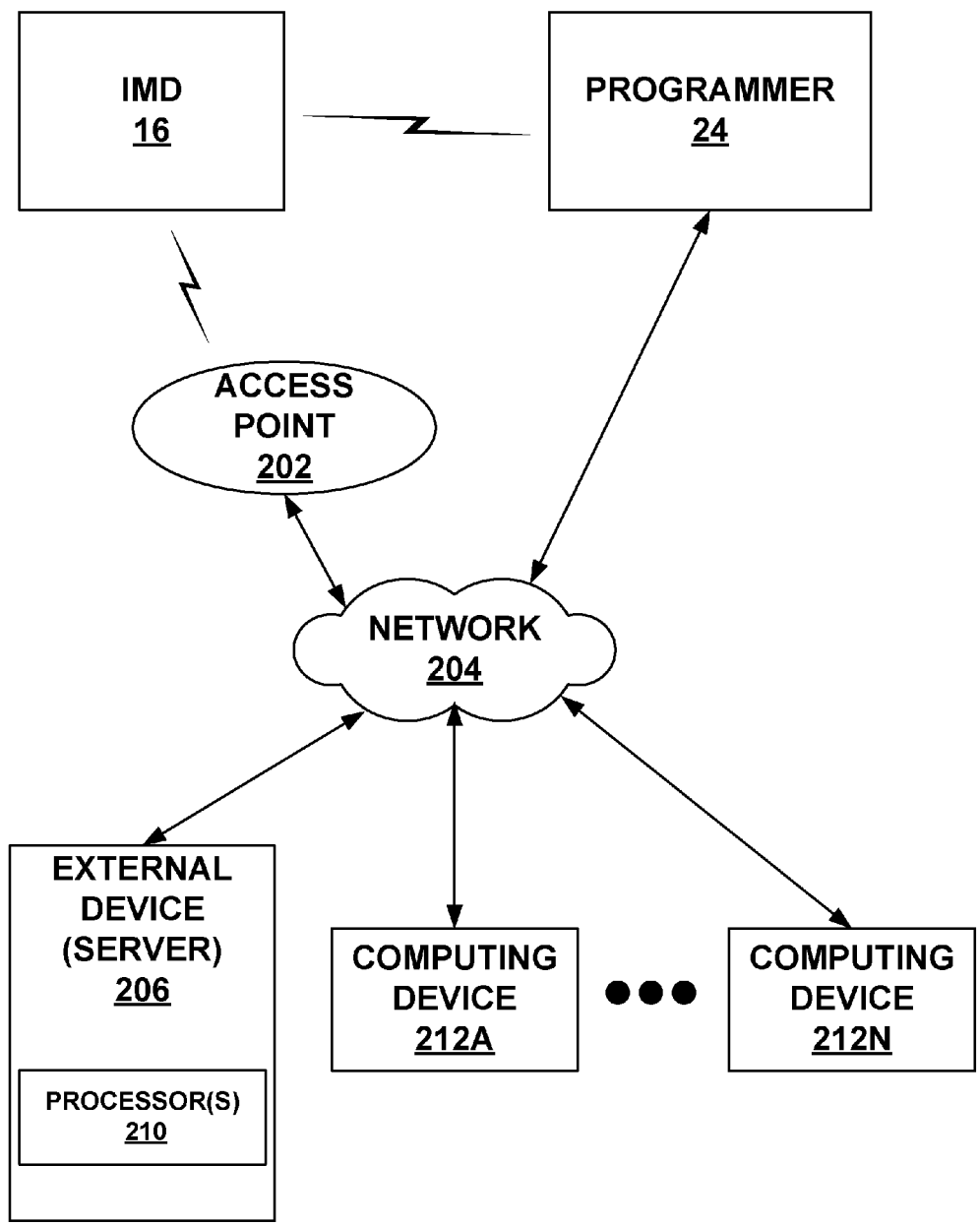
FIG. 5 is a block diagram illustrating an example system that includes an external device, such as a server, and one or more computing devices that are coupled to the IMD and programmer shown in FIG. 1 via a network.

FIG. 5 is a block diagram illustrating an example system that includes an external device, such as a server 206, and one or more computing devices 212A-212N that are coupled to the IMD 16 and programmer 24 shown in FIG. 1 via a network 204. Network 204 may be generally used to transmit diagnostic information (e.g., the occurrence of phrenic nerve stimulation) from an IMD 16 to a remote external computing device. In some examples, the heart sounds and/or EGM signals may be transmitted to an external device for processing.

In some examples, the IMD 16 transmits information during predetermined windows of time. In some examples, the windows of transmission align with a window during which an activation event may result in the initiation of a phrenic nerve detection sequence. In some examples, network 204 may also transmit information from IMD 16 regarding the activation event that triggered the phrenic nerve stimulation to the remote external computing device.

In some examples, the information transmitted by IMD 16 may allow a clinician or other healthcare professional to monitor patient 14 remotely. In some examples, IMD 16 may use its telemetry module 78 to communicate with programmer 24 via a first wireless connection, and to communicate with an access point 202 via a second wireless connection, e.g., at different times. In the example of FIG. 5, access point 202, programmer 24, server 206, and computing devices 212A-212N are interconnected, and able to communicate with each other, through network 204. In some cases, one or more of access point 202, programmer 24, server 206, and computing devices 212A-212 N may be coupled to network 204 via one or more wireless connections. IMD 16, programmer 24, server 206, and computing devices 212A-212N may each comprise one or more processors, such as one or more microprocessors, DSPs, ASICs, FPGAs, programmable logic circuitry, or the like, that may perform various functions and operations, such as those described herein.

Access point 202 may comprise a device that connects to network 204 via any of a variety of connections, such as telephone dial-up, digital subscriber line (DSL), or cable modem connections. In other examples, access point 202 may be coupled to network 204 through different forms of connections, including wired or wireless connections. In some examples, access point 202 may be co-located with patient 14 and may comprise one or more programming units and/or computing devices (e.g., one or more monitoring units) that may perform various functions and operations described herein. For example, access point 202 may include a home-monitoring unit that is co-located with patient 14 and that may monitor the activity of IMD 16. In some examples, server 206 or computing devices 212 may control or perform any of the various functions or operations described herein, e.g., determine, based on heart sounds, whether the phrenic nerve is being stimulated.

In some cases, server 206 may be configured to provide a secure storage site for archival of diagnostic information (e.g., occurrence of phrenic nerve stimulation and attendant circumstances such as pacing parameters) that has been collected and generated from IMD 16 and/or programmer 24. Network 204 may comprise a local area network, wide area network, or global network, such as the Internet. In some cases, programmer 24 or server 206 may assemble PNS information in web pages or other documents for viewing by and trained professionals, such as clinicians, via viewing terminals associated with computing devices 212. The system of FIG. 5 may be implemented, in some aspects, with general network technology and functionality similar to that provided by the Medtronic CareLink® Network developed by Medtronic, Inc., of Minneapolis, Minn.

In the example of FIG. 5, external server 206 may receive heart sound information from IMD 16 via network 204. Based on the heart sound information received, processor(s) 210 may perform one or more of the functions described herein with respect to signal analyzer 80 and processor 70. In some examples, an external device such as server 206 or computing devices 212 may provide an activation signal to IMD 16 via network 204. In response to the activation signal, IMD 16 may initiate a phrenic nerve detection sequence consistent with one or more of the methods described herein with respect to FIGS. 6-8, for example. In some examples, cardiac signals including EGM and heart sound signals are transmitted to the external device that sent the activation signal. The external device, such as server 206 processes the signals to determine whether phrenic nerve stimulation has occurred.

Figure 6:
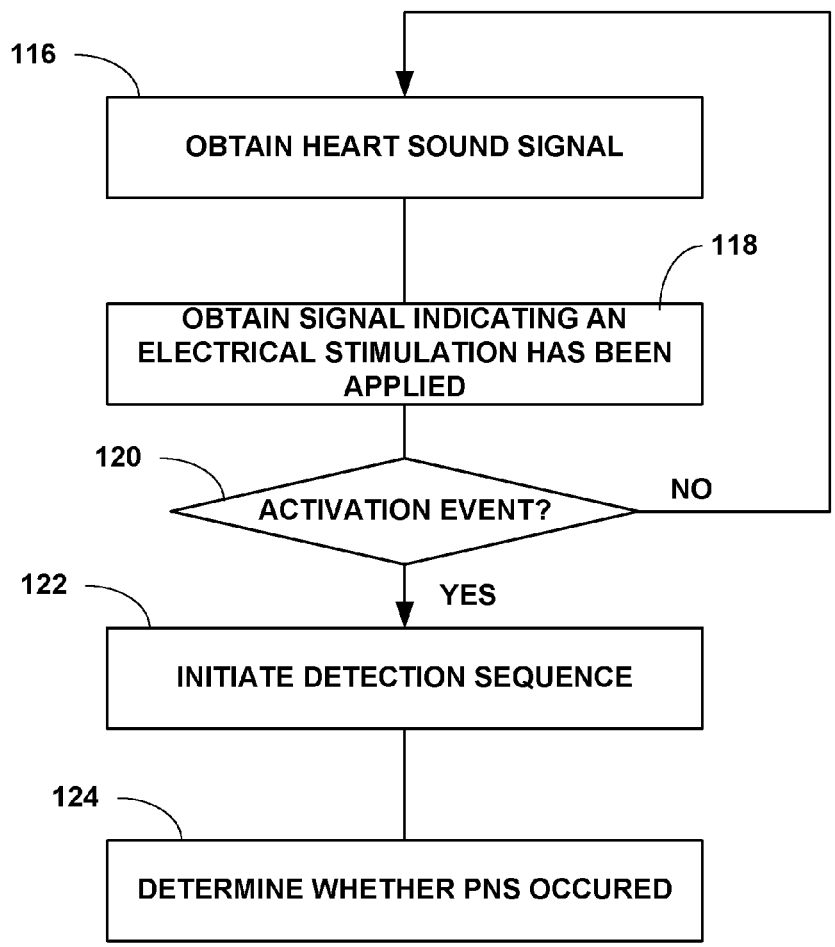
FIG. 6 is a flow chart illustrating an example mode of operation for determining if phrenic nerve stimulation has occurred, consistent with various examples of the present disclosure.

FIG. 6 is a flow chart illustrating an example mode of operation for determining if phrenic nerve stimulation has occurred, consistent with various examples of the present disclosure. IMD 16 obtains a heart sound signal (116). The heart sound signal may be obtained using heart sound sensor 82, for example. In some examples, the heart sound signal is continuously monitored by heart sound sensor 82. In some examples, the heart sound signal may be monitored by IMD 16 at predetermined intervals. IMD 16 may monitor other signals, including activity based, posture based, and EGM signals.

IMD may obtain a signal indicating an electrical stimulation has been applied (118). The indication may be derived from an EGM signal obtained by sensing module 76, for example. In some examples, the indication may come from signal generator 74 when the electrical stimulation is applied, or from a hardware element, software process, or state machine that controls delivery of stimulation by the signal generator.

In some examples, the electrical simulation is a cardiac electrical stimulation. For example, a pacing pulse or a defibrillating shock. In some examples, the electrical stimulation may be applied to the phrenic nerve with the purpose of stimulating the phrenic nerve and activating the diaphragm. In some examples, the electrical stimulation is applied by signal generator 74. In various examples, the indication that electrical stimulation has been applied may be received by processor 70.

As illustrated in FIG. 6, IMD 16 determines if an activation event (120) has occurred. In some examples, IMD 16 may receive an activation signal from a remote device. Processor 70 may activate phrenic nerve stimulation detection in response to an activation event such as receiving an activation signal. In some examples, one or more processors within IMD 16 may determine whether an activation event has occurred. For example, detection of an activation event may be based on information received from one or more of activity/posture sensor 84, memory 72, signal analyzer 80, signal generator 74, telemetry module 78 and sensing module 76. The processor 70 may determine an activation event has occurred based on information from the activity/posture sensor 84. For example, an activation event may be a low level of activity, indicating the patient 14 is at rest. In some examples, the activation event may be based on a signal from the activity/posture sensor 84 indicating the patient 14 is lying down. In certain more specific examples, the activation event may be an indication that the patient 14 is lying on his or her left side. In some examples, processor 70 may determine an activation event has occurred in response to a low activity level in combination with a posture-based signal indicating the patient 14 is lying down.

In various examples, the occurrence of an activation event may be determined based on information stored in memory 72. For example, the processor 70 may determine an activation event has occurred based on the time elapsed since the time of the previous phrenic nerve detection sequence, stored in memory 72. In some examples, memory 72 may store information regarding a time window during which an activation event may occur. For example, IMD 16 may be programmed to only allow for an activation event to result in activation of the phrenic nerve stimulation detection sequence from 10 p.m. to 5 a.m. In various examples, activation in response to an activation event may only occur during the window, and if an additional criteria is met. For example, the activity level may need to be below a certain level during the window before an activation event results in activation of the PNS detection sequence. In some examples, a posture-based signal generated by activity/posture sensor 84 must indicate patient 14 is lying down before processor 70 determines an activation event has occurred during the window.

In some examples, an activation event may be a change in pacing parameters applied by signal generator 74. Initiating a phrenic nerve stimulation detection sequence based on such an activation event may facilitate determining if the new pacing parameters stimulate one or more of phrenic nerves 36 and 38. In some examples, an activation event may be an indication from sensing module 76 or signal analyzer 80 that an abnormal EGM or heart sound signal has been received that may be indicative of phrenic nerve stimulation. The activation event results in the initiation of the phrenic nerve detection sequence in order to look specifically for phrenic nerve stimulation.

In some examples, an activation signal is received via telemetry module 78. The signal may be from a remote implantable device. For example, one or more activity or posture sensors may be implanted within patient 14. In some examples, the activation signal is received from a remote device such as programmer 24. Programmer 24 may provide an activation signal along with a change in pacing parameters to IMD 16. In other examples the activation signal may be provided in response to input from a clinician.

In the example operation illustrated in FIG. 6, a phrenic nerve stimulation detection sequence is initiated (122) in response to an activation event being detected by IMD 16. In examples where no activation event occurs IMD 16 maintains previous operating parameters. For example, IMD 16 may continue to monitor heart sound and EGM signals. IMD 16 may also continue to provide electrical pacing stimulation based on a set of pacing parameters. In some examples where the detection sequence is initiated, information regarding the occurrence of an activation event is provided to signal analyzer 80 by processor 70. In response to the activation event, signal analyzer 80 processes the heart sound signal obtained by heart sound sensor 82. In some examples, signal analyzer 80 processes an ensemble-averaged heart sound signal waveform, e.g., an average of the signals associated with a plurality of periods, such as a plurality of cardiac cycles. In certain more specific examples, the ensemble averaged heart sound signal is an average of signals from nine cardiac cycles.

In some examples, an averaged heart sound signal uses a heart sound signal recorded for a predetermined amount of time, for example 10 seconds, and aligns the heart sound signal cycles based on a reference point. In certain more specific examples, the reference point is the occurrence of a ventricular pacing pulse or an R-wave of an EGM signal. In some examples, the ventricular pacing reference point corresponds to time zero (0 ms) when pacing pulses are provided to the left ventricle at a heart rate of 60 beats per minute and an atrial paced AV delay of 140 ms.

In various examples, the ensemble-averaged heart sound waveform includes phrenic nerve stimulation artifacts. In some examples, signal analyzer 80 checks to determine if a pacing pulse is resulting in phrenic nerve stimulation. In such examples, signal analyzer 80 checks for the presence of phrenic nerve stimulation pulse within a window starting just after the ventricular pacing pulse or R-wave and ending before heart sound S1. In some examples, the window is approximately 80 ms in length and starts just after the ventricular pacing pulse.

In various examples the heart sound signal is sampled at a frequency of 256 Hz. In some examples, signal analyzer 80 comprises one or more band channels, each of which may include a band filtered sense-amplifier that compares the detected signal to a threshold. If the filtered and amplified signal is greater than the threshold, the narrow band channel indicates that phrenic nerve stimulation has occurred (124). In some examples, the band channel ranges from 50 Hz to 70 Hz. In some examples, a peak detector is used to determine if a spike in the heart sound signal has occurred within the window.

In some examples, signal analyzer 80 may compare a heart sound signal during the window to a heart sound template. In such examples, the presence of phrenic nerve stimulation may be determined using a template matching scheme that compares detected heart sounds to template heart sounds, such as a wavelet matching scheme or a "bounded template" matching scheme. An example wavelet template matching scheme is disclosed in U.S. Pat. No. 6,393,316 issued to Jeff Gillberg. An example bounded template matching scheme is disclosed in US Publication No. 20100185109, entitled "A Blurred Template Approach for Arrhythmia Detection," by Xin Zhang, Mark Brown, Xusheng Zhang, and Jeff Gillberg. The template may, for example, be a stored heart sound signal from patient 14 where no phrenic nerve stimulation is present that is loaded into signal analyzer 80 from memory 72. Signal analyzer 80 may determine whether phrenic nerve stimulation occurred (124) based on the difference between the template and the actual signal. In some examples, signal analyzer 80 looks at the heart sound signal provided by heart sound sensor 82 and checks each individual beat for the presence of a phrenic nerve stimulation artifact.

In examples where the electrical stimulation applied is intended to provide electrical stimulation to the phrenic nerve, signal analyzer 80 may focus on a different portion of the heart sound signal. In some examples, the phrenic nerve stimulation may be applied during the refractory period of the heart. Signal analyzer 80 may monitor the period between S1 and S2 to determine if the electrical stimulation was effective at stimulating one or more of phrenic nerves 36 and 38 and activating diaphragm 102. A variety of processing techniques may be used to determine whether phrenic nerve stimulation has occurred (124) including, those discussed above with respect to a window between the ventricular pacing pulse and heart sound S1.

In some examples, determination of phrenic nerve stimulation is confirmed by processor 70. For example, if a phrenic nerve stimulation artifact is detected using the heart sound signal by signal analyzer 80 for a particular set of pacing parameters, processor 70 may vary one or more pacing parameters. In certain examples, if phrenic nerve stimulation is detected at one AV delay setting, the presence of phrenic nerve stimulation may be confirmed by cross-checking the heart sound signals at different AV delay settings. The confirmation process is discussed in more detail below with respect to FIGS. 10 and 11.

In some examples, the PNS detection sequence of FIG. 6 is used to confirm successful therapeutic PNS. PNS may be desired to treat a variety of breathing disorders, including for example, sleep apnea. Purposeful PNS may be delivered at a rate lower than pacing stimulation. In general a person takes approximately 10 breathes a minute, while the heart beats more than 60 times a minute. Accordingly, purposeful PNS may occur at a rate significantly below that of paced or intrinsic heartbeats. This means that a number of cycles of EGM and heart sound signals may not include a PNS artifact despite effective PNS. In such examples, it may be beneficial to ensure that signal analyzer 80 analyzes a heart sounds signal during a time period including the delivery of an electrical stimulation pulse intended to provide PNS. In some examples, the PNS detection sequence is initiated in response to the application of the electrical signal.

Although FIG. 6 illustrates an example in which the determination of whether an activation event has been detected occurs after obtaining a heart sound signal (116) and obtaining a signal indicating an electrical stimulation has been applied (118), in various other examples the activation event may be detected by IMD 16 prior to one or more of obtaining a heart sound signal (116) and obtaining a signal indicating an electrical stimulation has been applied (118). In this manner, resources of IMD 16 or other devices associated with obtaining a heart sound signal or obtaining an indication of electrical stimulation may be conserved during periods in which no detection sequence is to be performed due to the absence of an activation event.

Figure 7:
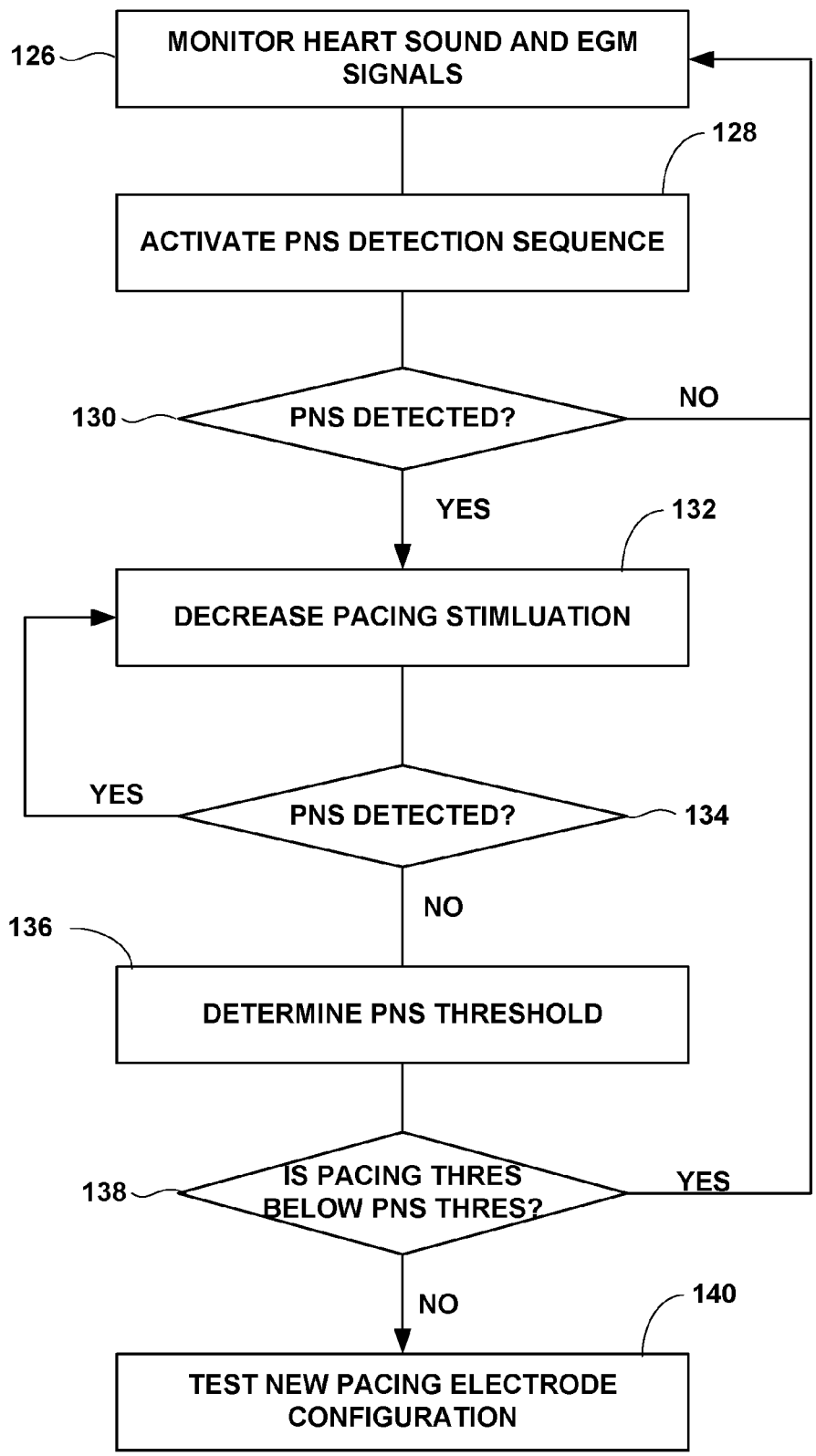
FIG. 7 is a flow chart illustrating an example mode of operation of an IMD consistent with the present disclosure.

FIG. 7 illustrates an example mode of operation of IMD 16 consistent with the present disclosure. IMD 16 monitors heart sound and EGM signals (126). In some examples, the heart sounds signal is monitored by heart sound sensor 82 and the EGM signal is monitored by sensing module 76. In various examples, the monitored heart sound and EGM signals may be used by IMD 16 for a variety of purposes. For example, the heart sound and EGM signals may be used by signal analyzer 80 to determine the effectiveness of a set of pacing parameters being used for cardiac resynchronization therapy (CRT).

IMD activates a phrenic nerve detection sequence (128). In some examples, the activation is in response to a change in the pacing parameters being applied to heart 12. In some examples, the phrenic nerve stimulation detection sequence may be activated at a particular time of day, or in response to a signal from the activity/posture sensor 84. In some examples, memory 72 provides a phrenic nerve stimulation detection program to signal analyzer 80 in response to an activation event detected by processor 70. In some examples, the detection of phrenic nerve stimulation is preformed as discussed with respect to FIG. 6, above.

If no PNS is detected (130) the IMD 16 continues to monitor heart sound and EGM signals (126). In some examples, the signal analyzer 80 may revert to a previous analyzing program when PNS is not detected. For example, signal analyzer 80 may analyze cardiac signals, including EGM signals or heart sounds signals for the presence of an arrhythmia.

If PNS is detected (130) then processor 70 may initiate a sequence to modify one or more of the pacing parameters to avoid the PNS, while still providing adequate pacing stimulation. In some examples, processor 70 modifies the pacing parameters applied by signal generator 74 by decreasing the amplitude of the pacing stimulation (132) by a predefined amount. Signal analyzer 80 processes a heart sound signal from heart sound sensor 82 that is obtained subsequent to the change in pacing stimulation. If PNS detected (134) then the processor 70 again decreases the pacing stimulation (132). This loop continues until PNS is no longer detected. Based on the amplitude level of the pacing stimulation at which PNS is not longer detected, IMD 16 determines a PNS threshold (136).

IMD 16 then determines if the pacing threshold (the amplitude of stimulation at which an action potential may be achieved) is below the PNS threshold (138). If the pacing threshold is below the PNS threshold, then processor 70 terminates the PNS detection sequence as well as the modification of pacing parameters and signal generator 74 applies the new set of pacing parameters including pacing at an amplitude between the pacing threshold and the PNS threshold. In some examples, IMD 16 continues to monitor heart sound and EGM signals (126).

In some examples, IMD 16 compares the PNS threshold and the pacing capture threshold, and if the difference between the two thresholds allows enough room to ensure regular pacing capture without phrenic nerve stimulation, then the pacing vector/electrode configuration is not changed. If however, the pacing threshold is not below the PNS threshold, or processor 70 determines there is not a large enough difference between the two, IMD 16 modifies the pacing vector/electrode configuration and tests a new pacing electrode configuration (140) for phrenic nerve stimulation. In some embodiments, IMD 16 also tests the effectiveness of the new electrode configuration.

Figure 8:
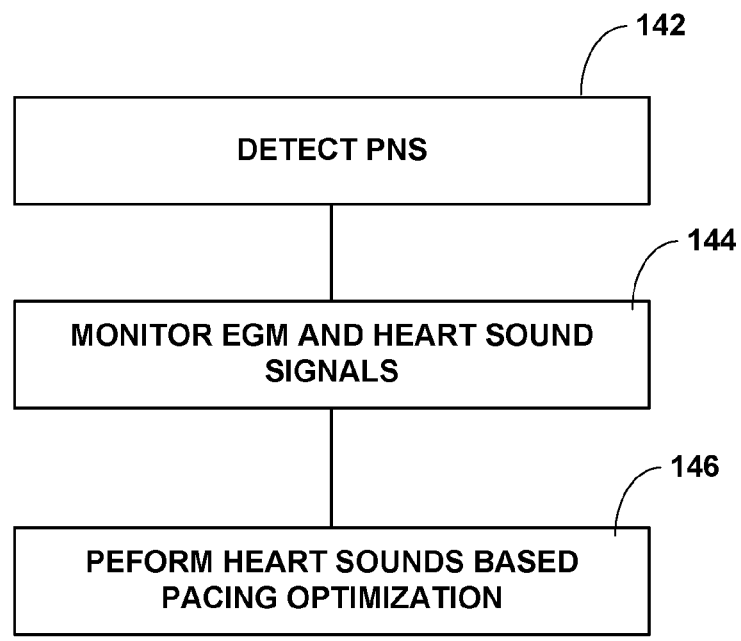
FIG. 8 is a flow chart illustrating an example operation sequence of an IMD, consistent with the present disclosure.

FIG. 8 illustrates an example operation sequence for IMD 16, consistent with the present disclosure. IMD 16 detects the presence of phrenic nerve stimulation (142). In various examples, phrenic nerve stimulation detection is performed by signal analyzer 80, consistent with the examples discussed with respect to FIG. 6. For example, the phrenic nerve stimulation detection sequence may be initiated in response to an activation event. The activation event may be a detected abnormality in the heart sounds signal. In some examples, it may be to a change in pacing parameters, or a signal from the activity/posture sensor 84. In some examples, the activation event may be an activation signal received by IMD 16 from an external device.

In response to the detection of phrenic nerve stimulation IMD 16 monitors EGM and heart sound signals (144). The signals from heart sound sensor 82 and sensing module 76 are used by signal analyzer 80 to perform heart sounds based pacing optimization (146). For more information regarding heart sounds-based pacing parameter optimization see U.S. patent application Ser. No. 13/111,260, to Zhang et al, entitled, "HEART SOUNDS-BASED PACING OPTIMIZATION," filed May 19, 2011, and assigned to Medtronic, and incorporated herein by reference. In various examples, signal analyzer 80 extracts a variety of heart sound features from the heart sound signals in addition to the phrenic nerve stimulation peak. These may include, for example, information regarding heart sounds S1-S4, including their relationship to one another as well at the amplitude and duration of each sound. In some examples, processor 70 may vary a number of pacing parameters over a predefined range, and compare the resulting heart sound and EGM signals to determine which set of pacing parameters results in a lack of phrenic nerve stimulation while still providing adequate heart function. In other examples, processor 70 chooses a set of pacing parameters based on the results that provides the best overall heart function while avoiding phrenic nerve stimulation.

Figure 9A:
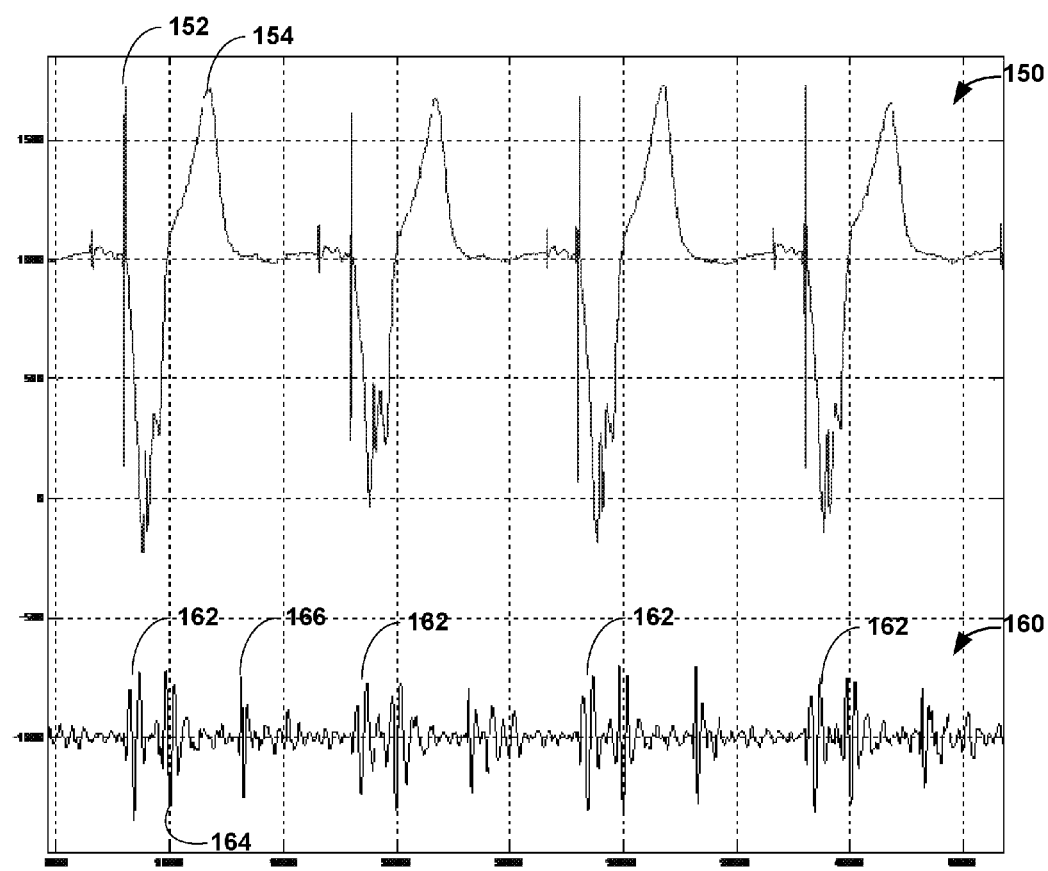
FIG. 9a illustrates an example EGM signal and an example heart sounds signal indicative of the presence of phrenic nerve stimulation.
Figure 9B:
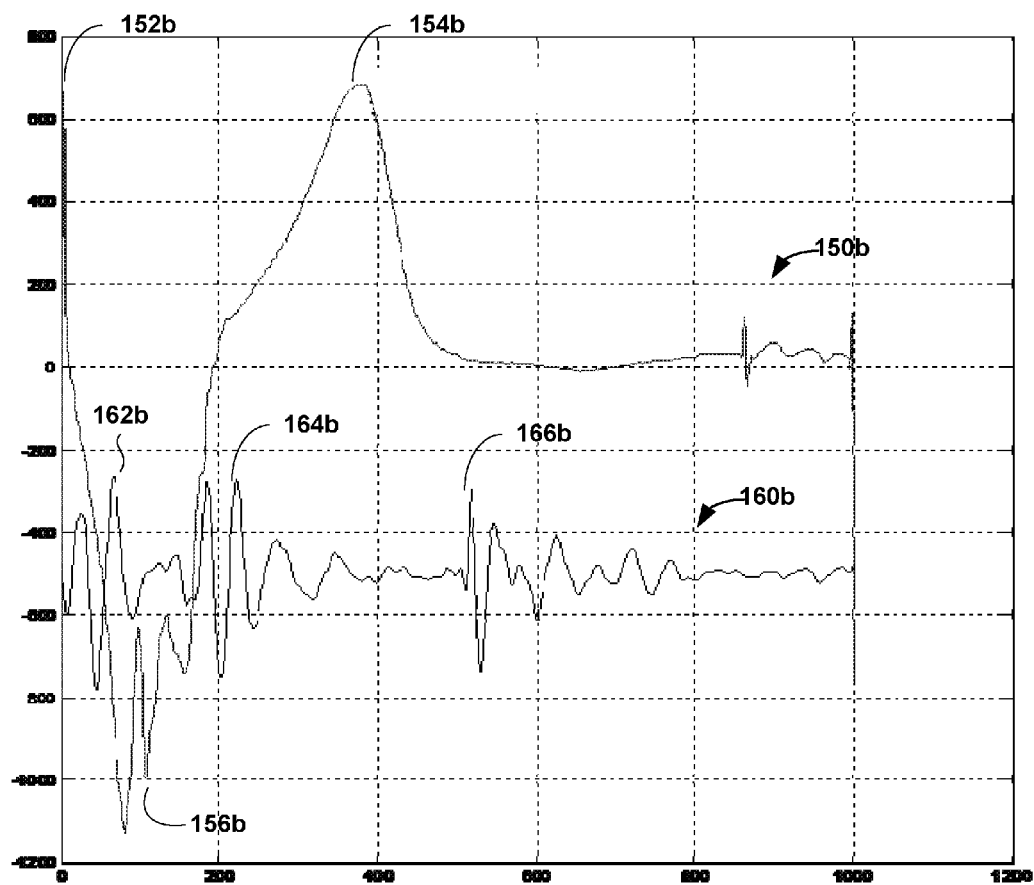
FIG. 9b illustrates ensemble-averaged example EGM and heart sound signals indicative of the presence of phrenic nerve stimulation.

FIGS. 9a and 9b illustrate EGM and heart sound signals indicative of the presence of phrenic nerve stimulation. EGM signal 150 may be detected by sensing module 76, for example. Heart sound signal 160 may be detected by heart sound sensor 82, for example. EGM signal 150 includes a spike 152 that represents the application of stimulation to the heart. In some examples, spike 152 is the ventricular pacing marker. R-wave 154 of EGM signal 150 aligns approximately with heart sound S1 164. Heart sound S2 166 occurs after heart sound S1 and after R-wave 154. Heart sound 162 indicates phrenic nerve stimulation. Heart sound 162 occurs after spike 152 and before heart sound S1 164.

The example EGM signal 150 and heart sound signal 160 represent the electrical and mechanical function of heart 12 under a set of pacing parameters wherein the AV delay is approximately 140 ms. FIG. 9a shows that the heart sound 162, also known as the PNS artifact consistently occurs approximately within 80 ms window after the application of the ventricular pacing marker.

FIG. 9b shows an ensemble-averaged EGM signal 150b and an ensemble-averaged heart sounds signal 160b. As shown in FIG. 9b, EGM signal 150b and heart sound signal 160b are waveforms representing the average of a plurality of segments of each of an EGM signal and a heart sounds signal, each segment corresponding to a respective cardiac cycle. In some examples, the number of cardiac cycles may be nine, and the heart rate may be between 59-61 beats per minutes. The pacing parameters and stimulation provide an AV delay of approximately 140 ms and a VV (inter-ventricular) delay of 0 ms. PNS artifact 162b occurs approximately within 80 ms window after the ventricular pacing marker 152b. Heart sound 164b is heart sound S1 and aligns approximately with the R-wave 154b of EGM signal 150b. Heart sound 166b is heart sound S2 and represents the closing of the semilunar valves of heart 12. Heart sound 164b is heart sound S1 and represents the closing of atrial and ventricular valves during systole.

In various examples consistent with the present disclosure, and in particular the modes of operation described with respect to FIG. 6-8, the signals of either FIG. 9a or FIG. 9b are processed by signal analyzer 80 and, based on the presence of heart sound 162, a determination is made that phrenic nerve stimulation has occurred. In other examples, the PNS artifact may be located in a different portion of the heart sound signal. For example, in instances where phrenic nerve stimulation is intentional, the phrenic nerve stimulation may be applied during the refractory period. In such instances the PNS artifact may appear later in the heart sound signal cycle. For example, the artifact may occur between heart sounds S1 and S2. Accordingly, depending on the purpose of the phrenic nerve stimulation detection, either to determine if unwanted stimulation is occurring or to confirm wanted stimulation, the portion of the heart sound signal studied by signal analyzer 80 may differ.

Figure 10:
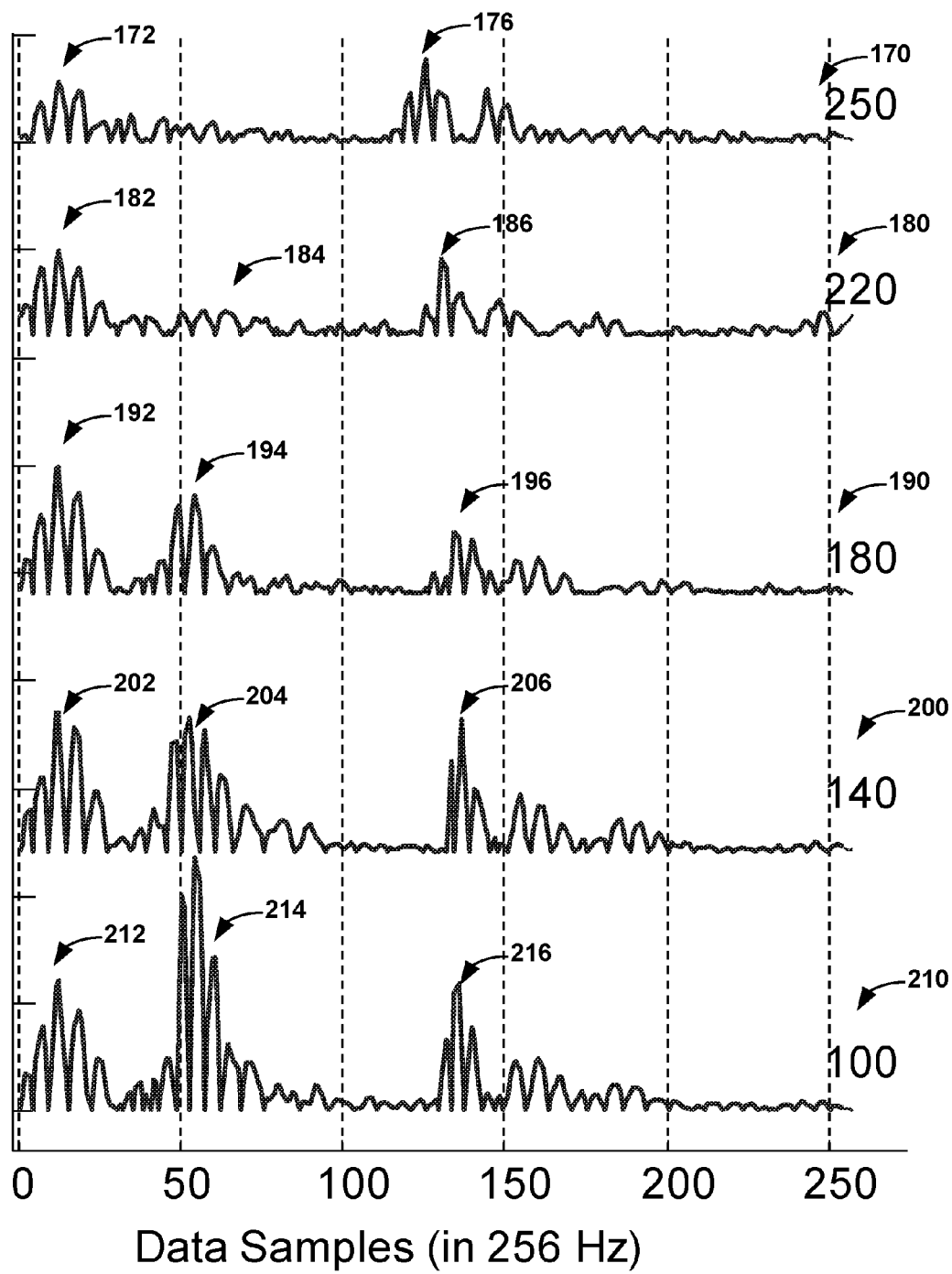
FIG. 10 illustrates heart sound signals including PNS artifacts at a variety of different AV delays.

FIG. 10 illustrates heart sound signals, which include PNS artifacts, and were obtained during pacing at a variety of different AV delays. As discussed above, monitoring and processing of heart sound signals obtained for a variety of different AV delays may be used to confirm the presence of phrenic nerve stimulation. As shown in FIG. 10, the AV delay was varied over a range from 100 ms to 250 ms.

Heart sound signal 170 was obtained at an AV delay of 250. The PNS artifact 172 is present, as is heart sound 176, which is heart sound S2. Heart sound signal 170 corresponds to a heart that is not functioning properly. The phrenic nerve stimulation may be affecting the hemodynamics of the heart 12.

Heart sound signal 180 was obtained from pacing parameters resulting in an AV delay of 220 ms. PNS artifact 182 is present, as well as a small indication of heart sound S1 at heart sound 184. Heart sound 186 is heart sound S2.

Heart sound signal 190 was obtained at an AV delay of 180 ms. PNS artifact 192 is present as well as heart sound 194, which is heart sound S1 and heart sound 196, which is heart sound S2. Heart sound signal 200 includes PNS artifact 202, heart sound 204, which is heart sound S1 and heart sound 206, which is heart sound S2. Heart sound signal 200 was obtained at an AV delay of 140 ms. Heart sound signal 210 was obtained at an AV delay of 100 ms and includes heart sound signals 212, 214 and 216 which represent PNS artifact, heart sound S1, and heart sound S2, respectively.

As shown in this graph, although the various AV delays may change the characteristics of each heart sound, the PNS artifact is present at all AV delays. Cycling through a number of AV delays may be helpful to confirm the presence of pacing-induced phrenic nerve stimulation.

Figure 11:
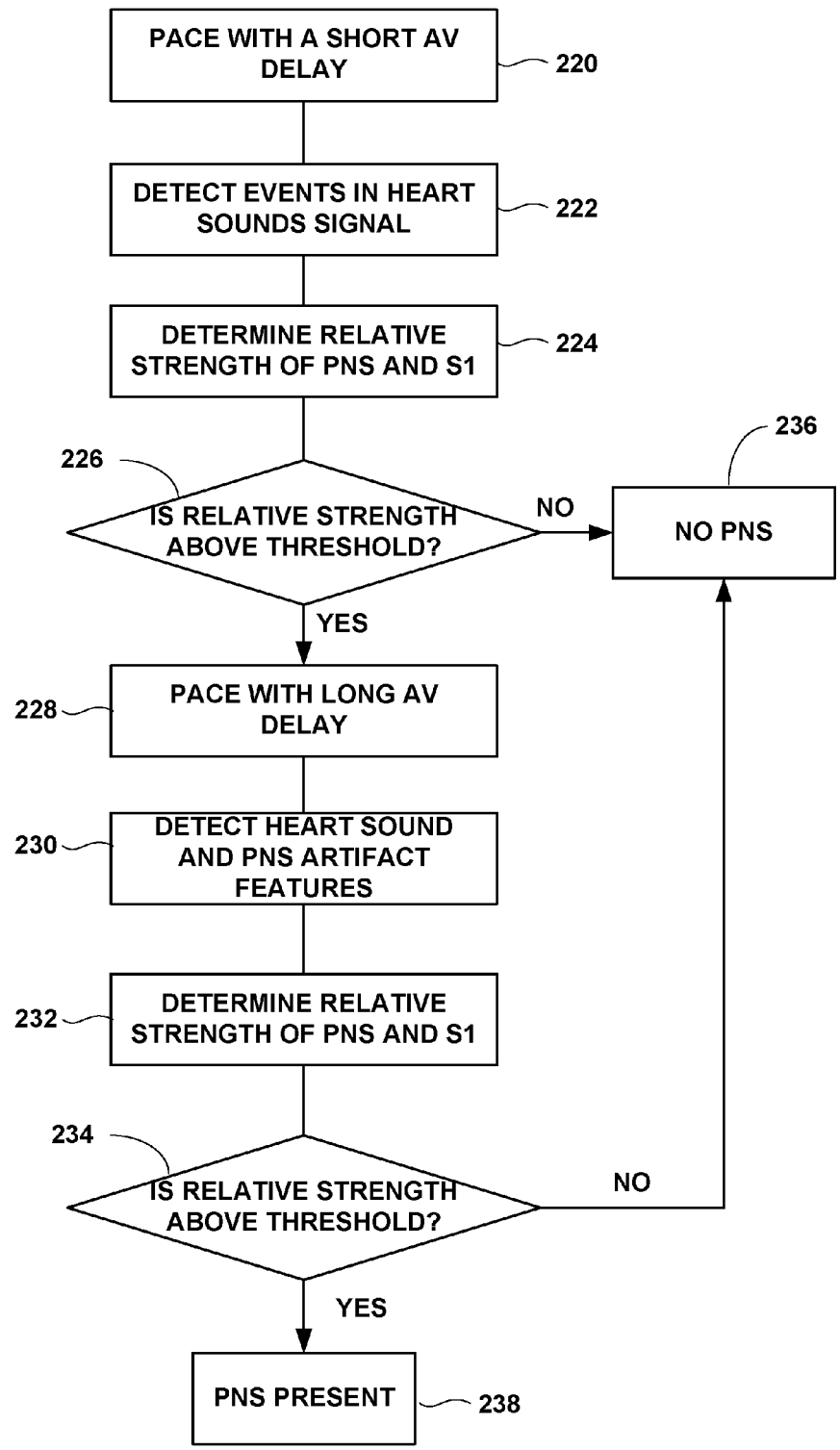
FIG. 11 illustrates a method of confirming the presence of PNS at a plurality of AV delays.

FIG. 11 illustrates a method of confirming the presence of PNS at a plurality of AV delays. In response to an activation event, such as a time window, IMD 16, via signal generator 74 provides pacing with a short AV delay (220). In some examples the short AV delay is the AV delay at which pacing was being applied prior to the activation event. In some examples, the short AV delay may be approximately 70 ms.

Signal analyzer 80, for example, is used to detect events in a heart sounds signal, e.g., heart sounds and PNS artifacts, and determines features of the heart sounds and PNS artifacts (222). In some examples, signal analyzer 80 analyzes a heart sound signal from heart sound sensor 82 as well as an EGM signal from sensing module 76. In some examples, signal analyzer 80 analyzes an EGM-gated heart sounds signal ensemble averaged over N beats. In some examples, N may be approximately 5 to 10 beats.

Signal analyzer 80 detects at least two heart sound features, S1 amplitude and PNS amplitude. In some examples, the presence of PNS is determined by monitoring a portion of the heart sounds signal between the application of a pacing pulse and S1. Based on the amplitudes of S1 and PNS, IMD determines the relative strength of the PNS and S1 heart sounds (224). In some examples, the PNS amplitude is divided by the S1 amplitude. IMD 16 then determines whether the relative strength of PNS amplitude to S1 amplitude is above a predetermined threshold (226). In some examples the threshold may be approximately 0.3.

If the relative strength of the PNS amplitude to S2 amplitude is below the threshold, then no PNS is present (236) and the detection sequence is terminated. If the relative strength is above the threshold, then the AV delay is modified, and IMD 16 provides stimulation to heart 12. The IMD 16 provides pacing with a long AV delay (228). In some examples, the long AV delay may be approximately the intrinsic AV delay minus 20 ms. In some examples, the intrinsic AV delay is determined by the interval between Asense and Vsense, where Asense is a result of the depolarization of the atrium and Vsense is the result of the depolarization of the ventricle. In some examples the intrinsic AV delay is determined by the interval between Apace and Vsense, where Apace is the application of electrical stimulation to the atrium.

Signal analyzer 80 again detects heart sound and PNS artifact features (230). The heart sound signals and EGM signals used in the signal analysis are a result of the longer AV delay during pacing. In one example, signal analyzer 80 determines PNS artifact amplitude and S1 amplitude. IMD 16 then determines a relative strength of the PNS amplitude and the S1 amplitude (232). IMD 16 then determines if the relative strength of PNS amplitude and S1 amplitudes is above a threshold (234). In some examples, the threshold used during long AV delay pacing is the same as during short AV delay pacing. If the relative strength is not above the threshold then no PNS is present (236). If the relative strength is above the threshold, then PNS is present (238). The PNS detection sequence is then terminated. In some examples, at least two of the signals shown in FIG. 10 results from a PNS detection sequence consistent with the method of FIG. 11.

IMD 16 may respond to a determination of whether PNS is present in a variety of ways. In some examples, PNS detection may result in a modification to a set of pacing parameters. In some examples, the PNS may be desired, and the lack of PNS may result in a modification to one or more parameters electrical stimulation for causing PNS. For example, an IMD may increase the amplitude or pulse width of a signal delivered to the peripheral nerves, or select a different electrode combination for delivery of the signal, in response to a determination of lack of PNS. In some examples, IMD 16 provide an indication that PNS is present or absent to external programmer 24 or network 204 via telemetry module 78.

Various examples have been described. These and other examples are within the scope of the following claims.

The invention claimed is:

1. A method of detecting phrenic nerve stimulation in a patient comprising:
    detecting an activation event;
    obtaining a heart sound signal of a patient from an implanted heart sound sensor;
    determining that an electrical stimulation has been applied to the patient; in response to detecting the activation event, monitoring a portion of the heart sound signal, the portion defined by a predetermined window after the application of the electrical stimulation;
    determining whether phrenic nerve stimulation occurred based on the portion of the heart sound signal;
    determining that the phrenic nerve has been stimulated; and
    in response to the determination that the phrenic nerve has been stimulated:
    changing an atrioventricular delay of cardiac pacing; and
    confirming the determination that the phrenic nerve has been stimulated by at least monitoring another portion of the heart sound signal, the portion defined by another predetermined window after the application of the cardiac pacing at the changed atrioventricular delay.

2. The method of claim 1, wherein the electrical stimulation comprises cardiac pacing, the further comprising:
    determining a phrenic nerve stimulation threshold;
    determining a cardiac pacing capture threshold;
    comparing the phrenic nerve stimulation threshold and the cardiac pacing capture threshold; and
    based on the comparison, setting a cardiac pacing amplitude.

3. The method of claim 2, further including changing a pacing vector for the cardiac pacing when the comparison of the phrenic nerve stimulation threshold and the cardiac pacing capture threshold indicates that the cardiac pacing capture threshold is above the phrenic nerve stimulation threshold.

4. The method of claim 3, further including determining if the changed pacing vector causes phrenic nerve stimulation.

5. The method of claim 1, wherein the electrical stimulation comprises a cardiac pacing pulse.

6. The method of claim 1, wherein the electrical stimulation is delivered via an intracardiac lead.

7. The method of claim 1, wherein detecting the activation event comprises one or more of:
- detecting at least one of a posture or position of the patient based on information from a posture sensor;
- detecting that the patient is lying on a left side of the patient;
- detecting an indication of a low level of patient activity from a patient activity sensor;
- detecting the activation event comprising detecting a predetermined time window; and
- detecting a change in a set of parameters of the cardiac pacing.

8. The method of claim 1, wherein the predetermined window is defined by the application of the electrical stimulation and heart sound S1.

9. The method of claim 1, further comprising:
- determining a first relative strength of a phrenic nerve stimulation artifact and heart sound S1;
- comparing the first relative strength to a predetermined threshold;
- based on the comparison of the first relative strength to the predetermined threshold, determining whether phrenic nerve stimulation has occurred;
- determining a second relative strength of a phrenic nerve artifact and heart sound S1 at the changed atrioventricular delay;
- comparing the second relative strength to the predetermined threshold; and
- based on the comparison of the second relative strength to the predetermined threshold, confirming the determination of whether phrenic nerve stimulation has occurred.

10. The method of claim 1, wherein the heart sound signal is ensemble averaged.

11. A system for detecting phrenic nerve stimulation, the system comprising:
- an implantable heart sound sensor configured to obtain a heart sound signal;
- a processor configured to detect an activation event;
- a signal analyzer configured to:
- receive the heart sound signal;
- obtain a signal indicating an electrical stimulation has been applied; and
- in response to the processor detecting the activation event, monitor a portion of the heart sound signal, the portion defined by a predetermined window after an applied stimulation; and
- the processor further configured to determine whether phrenic nerve stimulation occurred based on the portion of the heart sound signal, wherein the processor is further configured to, in response to a determination that the phrenic nerve has been stimulated, confirm the determination via a change in atrioventricular delay resulting from the electrical stimulation.

12. The system of claim 11, wherein the processor is further configured to:
- determine a phrenic nerve stimulation threshold;
- determine a cardiac pacing capture threshold;
- compare the phrenic nerve stimulation threshold and the cardiac pacing capture threshold, and
- based on the comparison set a cardiac pacing amplitude.

13. The system of claim 12, wherein the processor is further figured to change a pacing vector used by a signal generator when the comparison of the phrenic nerve stimulation threshold and the cardiac pacing capture threshold indicates that the cardiac pacing capture threshold is above the phrenic nerve stimulation threshold.

14. The system of claim 13, wherein the signal analyzer is further configured to determine if the changed pacing vector causes phrenic nerve stimulation.

15. The system of claim 11, wherein the electrical stimulation comprises a cardiac pacing pulse.

16. The system of claim 11, further including an intracardiac lead configured to deliver the electrical stimulation.

17. The system of claim 11, further comprising at least one of a posture sensor, an activity sensor, and a signal generator, and wherein detecting the activation event comprises one or more of:
- detecting at least one of posture or position of the patient based on information from the posture sensor;
- detecting that the patient is lying on a left side of the patient;
- detecting an indication of a low level of activity from the patient activity sensor;
- detecting a predetermined time window; and
- detecting a change in a set of pacing parameters used by the signal generator to generate cardiac pacing stimuli.

18. The system of claim 11, wherein the predetermined window is defined by the application of the electrical stimulation and heart sound S1.

19. The system of claim 11, wherein the processor is further configured to:
- determine a first relative strength of a phrenic nerve stimulation artifact and heart sound S1;
- compare the first relative strength to a predetermined threshold;
- based on the comparison of the first relative strength to the predetermined threshold, determine whether phrenic nerve stimulation has occurred;
- determine a second relative strength of a phrenic nerve artifact and heart sound S1 at the changed atrioventricular delay;
- compare the second relative strength to the predetermined threshold;
- based on the comparison of the second relative strength to the predetermined threshold, confirm the determination of whether phrenic nerve stimulation has occurred.

20. The system of claim 11, further comprising an implantable medical device comprising a housing that houses the implantable heart sound sensor, the signal analyzer, and the processor, wherein the implantable medical device further comprises a signal generator configured to deliver cardiac pacing, and wherein the electrical stimulation comprises the cardiac pacing.

21. The system of claim 11, wherein the processor is further configured to ensemble average the heart sound signal.

22. A non-transitory computer-readable medium storing instructions which cause a medical device system to perform a method comprising:
- detecting an activation event;
- obtaining a heart sound signal of a patient from an implanted heart sound sensor;
- determining that an electrical stimulation has been applied to the patient;
- in response to detecting the activation event, monitoring a portion of the heart sound signal, the portion defined by a predetermined window after the application of the electrical stimulation;

determining whether phrenic nerve stimulation occurred based on the portion of the heart sound signal;

determining that the phrenic nerve has been stimulated; and in response to the determination that the phrenic nerve has been stimulated:

changing an atrioventricular delay of cardiac pacing; and confirming the determination that the phrenic nerve has been stimulated by at least monitoring another portion of the heart sound signal, the portion defined by another predetermined window after the application of the cardiac pacing at the changed atrioventricular delay.

* * * * *

UNITED STATES PATENT AND TRADEMARK OFFICE
CERTIFICATE OF CORRECTION

| | | |
|---|---|---|
| PATENT NO. | : 8,876,727 B2 | Page 1 of 1 |
| APPLICATION NO. | : 13/474041 | |
| DATED | : November 4, 2014 | |
| INVENTOR(S) | : Xusheng Zhang et al. | |

It is certified that error appears in the above-identified patent and that said Letters Patent is hereby corrected as shown below:

In the Claims

Column 20, Line 56, Claim 2: Replace "cardiac pacing, the further comprising:" with -- cardiac pacing, further comprising: --

Column 21, Lines 48, 49, Claim 11: Replace "electrical stimulation has been applied; and" with -- electrical stimulation has been applied; --

Column 21, Line 67, Claim 12: Replace "based on the comparison set a cardiac pacing" with -- based on the comparison, set a cardiac pacing --

Column 22, Lines 42, 43, Claim 19: Replace "strength to the predetermined threshold;" with -- strength to the predetermined threshold; and --

Signed and Sealed this
Nineteenth Day of September, 2017

Joseph Matal
*Performing the Functions and Duties of the*
*Under Secretary of Commerce for Intellectual Property and*
*Director of the United States Patent and Trademark Office*